US012702662B2

(12) United States Patent
Hayden et al.

(10) Patent No.: US 12,702,662 B2
(45) Date of Patent: Aug. 11, 2026

(54) USE OF PRIDOPIDINE AND ANALOGS FOR TREATING RETT SYNDROME

(71) Applicant: PRILENIA NEUROTHERAPEUTICS LTD., Yakum (IL)

(72) Inventors: Michael Hayden, Yakum (IL); Michal Geva, Even-Yehuda (IL)

(73) Assignee: Prilenia Neurotherapeutics Ltd., Yakum (IL)

( * ) Notice: Subject to any disclaimer, the term of this patent is extended or adjusted under 35 U.S.C. 154(b) by 406 days.

(21) Appl. No.: 18/253,221

(22) PCT Filed: Nov. 19, 2021

(86) PCT No.: PCT/IL2021/051383
§ 371 (c)(1),
(2) Date: May 17, 2023

(87) PCT Pub. No.: WO2022/107146
PCT Pub. Date: May 27, 2022

(65) Prior Publication Data
US 2023/0414596 A1 Dec. 28, 2023

Related U.S. Application Data

(63) Continuation-in-part of application No. 17/498,075, filed on Oct. 11, 2021, now abandoned, and a (Continued)

(51) Int. Cl.
*A61K 31/451* (2006.01)
*A61K 31/4418* (2006.01)
(Continued)

(52) U.S. Cl.
CPC ........ *A61K 31/451* (2013.01); *A61K 31/4418* (2013.01); *A61K 31/4545* (2013.01); *A61P 25/00* (2018.01)

(58) Field of Classification Search
None
See application file for complete search history.

(56) References Cited

U.S. PATENT DOCUMENTS 4,923,459 A 5/1990 Kyojiro et al.
6,903,120 B2 6/2005 Svan et al.
(Continued)

FOREIGN PATENT DOCUMENTS

WO WO 2001/046144 A1 6/2001
WO WO 2001/046145 A1 6/2001
(Continued)

OTHER PUBLICATIONS

Amaral et al. "TRPC channels as novel effectors of BDNF signaling: Potential implications for Rett syndrome" Pharmacology & therapeutics. Feb. 2007;113(2):394.
(Continued)

*Primary Examiner* — Jeffrey S Lundgren
*Assistant Examiner* — Anthony Joseph Seitz
(74) *Attorney, Agent, or Firm* — Mark S. Cohen; PEARL COHEN LLP

(57) ABSTRACT

The subject invention provides a method for treating a subject afflicted with Rett syndrome comprising administering to the subject a pharmaceutical composition comprising pridopidine or pharmaceutical acceptable salts and at least one of compounds 1-8 or pharmaceutical acceptable salt thereof disclosed herein, so as to thereby treat the subject.

27 Claims, 14 Drawing Sheets

Specification includes a Sequence Listing.

Related U.S. Application Data continuation-in-part of application No. 16/952,123, filed on Nov. 19, 2020, now Pat. No. 12,102,627.

(51) Int. Cl.
*A61K 31/4545* (2006.01)
*A61P 25/00* (2006.01)

(56) References Cited

U.S. PATENT DOCUMENTS

| | | | | |
|---|---|---|---|---|
| 7,417,043 | B2 | 8/2008 | Svan et al. | |
| 7,579,474 | B2 | 8/2009 | Sonesson et al. | |
| 7,923,459 | B2 | 4/2011 | Gauthier et al. | |
| 9,006,445 | B2 | 4/2015 | Sonesson et al. | |
| 9,012,476 | B2 | 4/2015 | Zimmermann et al. | |
| 9,139,525 | B2 | 9/2015 | Wikström | |
| RE46,117 | E | 8/2016 | Sonesson et al. | |
| 9,796,673 | B2 | 10/2017 | Wu et al. | |
| 9,814,706 | B2 | 11/2017 | Zimmermann et al. | |
| 10,047,049 | B2 | 8/2018 | Barel et al. | |
| 10,130,621 | B2 | 11/2018 | Schmidt et al. | |
| 10,322,119 | B2 | 6/2019 | Bassan et al. | |
| 10,406,145 | B2 | 9/2019 | Schmidt et al. | |
| 11,141,412 | B2 * | 10/2021 | Schmidt | A61P 25/14 |
| 12,102,627 | B2 * | 10/2024 | Geva | A61P 25/14 |
| 2006/0135531 | A1 | 6/2006 | Sonesson et al. | |
| 2007/0238878 | A1 | 10/2007 | Desmond et al. | |
| 2007/0238879 | A1 | 10/2007 | Gauthier et al. | |
| 2010/0076024 | A1 | 3/2010 | Zimmermann et al. | |
| 2010/0105736 | A1 | 4/2010 | Wikström | |
| 2010/0197712 | A1 | 8/2010 | Carlsson et al. | |
| 2011/0206782 | A1 | 8/2011 | Zhang et al. | |
| 2013/0150406 | A1 | 6/2013 | Zimmermann et al. | |
| 2013/0197031 | A1 | 8/2013 | Sonesson | |
| 2013/0267552 | A1 | 10/2013 | Waters et al. | |
| 2014/0088140 | A1 | 3/2014 | Hayden et al. | |
| 2014/0088144 | A1 | 3/2014 | Egan | |
| 2014/0088145 | A1 | 3/2014 | Hayden et al. | |
| 2015/0202302 | A1 | 7/2015 | Licht et al. | |
| 2015/0209346 | A1 | 7/2015 | Hayden et al. | |
| 2015/0216850 | A1 | 8/2015 | Hayden et al. | |
| 2015/0374677 | A1 | 12/2015 | Schmidt et al. | |
| 2016/0095847 | A1 | 4/2016 | Sonesson et al. | |
| 2016/0166559 | A1 | 6/2016 | Sonesson et al. | |
| 2016/0243098 | A1 | 8/2016 | Geva et al. | |
| 2017/0020854 | A1 | 1/2017 | Licht et al. | |
| 2017/0022158 | A1 | 1/2017 | Barel et al. | |
| 2017/0266170 | A1 | 9/2017 | Waters et al. | |
| 2018/0055832 | A1 | 3/2018 | Hayden et al. | |
| 2018/0235950 | A1 | 8/2018 | Sonesson et al. | |
| 2019/0015401 | A1 | 1/2019 | Sonesson | |
| 2019/0030016 | A1 | 1/2019 | Schmidt et al. | |
| 2019/0046516 | A1 | 2/2019 | Russ et al. | |
| 2019/0192496 | A1 | 6/2019 | Hayden et al. | |
| 2019/0209542 | A1 | 7/2019 | Licht et al. | |
| 2019/0231768 | A1 | 8/2019 | Geva et al. | |
| 2019/0336488 | A1 | 11/2019 | Hayden et al. | |
| 2019/0350914 | A1 | 11/2019 | Geva et al. | |
| 2019/0350915 | A1 | 11/2019 | Bassan et al. | |
| 2020/0030308 | A1 | 1/2020 | Schmidt et al. | |
| 2021/0106572 | A1 | 4/2021 | Geva et al. | |
| 2022/0023280 | A1 * | 1/2022 | Schmidt | C07D 211/42 |
| 2022/0062255 | A1 | 3/2022 | Geva et al. | |
| 2023/0165849 | A2 | 6/2023 | Geva et al. | |

FOREIGN PATENT DOCUMENTS

| | | | |
|---|---|---|---|
| WO | WO 2005/121092 | A1 | 12/2005 |
| WO | WO 2006/040155 | A1 | 4/2006 |
| WO | WO 2008/127188 | A1 | 10/2008 |
| WO | WO 2009/074607 | A1 | 6/2009 |
| WO | WO 2011/054759 | A1 | 5/2011 |
| WO | WO 2011/107583 | A1 | 9/2011 |
| WO | WO 2012/002863 | A1 | 3/2012 |
| WO | WO 2013/027188 | A1 | 2/2013 |
| WO | WO 2013/034622 | A1 | 3/2013 |
| WO | WO 2013/086425 | A1 | 6/2013 |
| WO | WO 2013/152105 | A1 | 10/2013 |
| WO | WO 2014/195322 | A1 | 12/2014 |
| WO | WO 2014/205229 | A1 | 12/2014 |
| WO | WO 2015/112601 | A1 | 7/2015 |
| WO | WO 2016/003919 | A1 | 1/2016 |
| WO | WO 2016/138130 | A1 | 9/2016 |
| WO | WO 2016/138135 | A1 | 9/2016 |
| WO | WO 2017/015609 | A1 | 1/2017 |
| WO | WO 2017/015615 | A1 | 1/2017 |
| WO | WO 2017/147366 | A1 | 8/2017 |
| WO | WO 2018/039475 | A1 | 1/2018 |
| WO | WO 2018/039477 | A1 | 1/2018 |
| WO | WO 2018/053275 | A1 | 3/2018 |
| WO | WO 2018/053280 | A1 | 3/2018 |
| WO | WO 2018/053287 | A1 | 3/2018 |
| WO | WO 2018/136600 | A1 | 7/2018 |
| WO | WO 2019/036358 | A1 | 2/2019 |
| WO | WO 2019/046568 | A1 | 3/2019 |
| WO | WO 2019/050775 | A1 | 3/2019 |
| WO | WO 2020/188558 | A1 | 9/2020 |
| WO | WO 2020/250234 | A1 | 12/2020 |

OTHER PUBLICATIONS

Bates et al. "Huntington disease" Nature reviews Disease primers. Apr. 23, 2015;1(1):1-21.

Bermack et al. "The role of sigma receptors in depression" Journal of pharmacological sciences. Mar. 2005;97(3):317-36.

Briefs, B. (Apr. 2010) "Trial watch: NeuroSearch's dopaminergic stabilizer improves movement disorders in Huntington's disease" Nature Reviews Drug Discovery 9, 260.

Cheng et al. "Relationship between the inhibition constant (K1) and the concentration of inhibitor which causes 50 per cent inhibition (I50) of an enzymatic reaction" Biochemical pharmacology. Dec. 1, 1973;22(23):3099-108.

CSID:25948790, www.chemspider.com/Chemical-Structure.25948790.html (accessed 23:27, Jul. 15, 2016).

CSID:7971505, www.chemspider.com/Chemical-Structure.7971505.html (accessed 23:33, Jul. 15, 2016).

Database PubChem [Online] U.S. National Library of medicine; Oct. 11, 2011, XP002775774, Database accession No. CID53379489.

De Yebene et al. (2011). "Pridopidine for the treatment of motor function in patients with Huntington's disease (MermaiHD): a phase 3, randomised, double-blind, placebo-controlled trial" *The Lancet Neurology*, 10(12), 1049-1057.

Dyhrin et al. (2010). "The dopaminergic stabilizers pridopidine (ACR16) and (−)-OSU6162 display dopamine D2 receptor antagonism and fast receptor dissociation properties" European journal of pharmacology, 628(1-3), 19-26.

European Search Report and Written Opinion, mailed Dec. 8, 2017 in connection with EP Application No. 15814023.6.

Geva et al. "Pridopidine activates neuroprotective pathways impaired in Huntington Disease" Human Molecular Genetics. Sep. 9, 2016;25(18):3975.

Geva et al. "Pridopidine Treatment Recovers Gait Abnormalities and Rescues Impaired BDNF Expression in a Rett Syndrome Mouse Model" 2018 (P3. 324).

Goodman, LaVonne "Huntington's Disease Drug Works" (Feb. 16, 2010)—ACR-16 (Huntexil). Trial Results: Good News from Europe.

Guy et al. "A mouse Mecp2-null mutation causes neurological symptoms that mimic Rett syndrome" Nature genetics. Mar. 2001;27(3):322-6.

Huntington Study Group HART Investigators. (2013). A randomized, double-blind, placebo-controlled trial of pridopidine in Huntington's disease. Movement Disorders, 28(10), 1407-1415.

International Search Report for PCT Application No. PCT/IL2021/051383 dated Feb. 17, 2022.

International Search Report for PCT Application No. PCT/US2015/038349 dated Sep. 30, 2015.

International Search Report for PCT Application No. PCT/US2017/051803 dated Dec. 22, 2017.

(56) References Cited

OTHER PUBLICATIONS

Isaias et al. "Gait initiation in children with Rett syndrome" PloS one. Apr. 17, 2014;9(4):e92736.
Johansson et al. (2012). "Placebo-controlled cross-over study of the monoaminergic stabiliser (−)-OSU6162 in mental fatigue following stroke or traumatic brain injury" Acta Neuropsychiatrica, 24(5), 266-274.
Johnston et al. "Pridopidine, a clinic-ready compound, reduces 3, 4-dihydroxyphenylalanine-induced dyskinesia in Parkinsonian macaques" Movement disorders: official journal of the Movement Disorder Society. May 2019;34(5):708-16.
Katz DM. "Brain-derived neurotrophic factor and Rett syndrome" Handbook of experimental pharmacology. 2014;220:481-95.
Mueller BH. "Neuroprotective properties of sigma-1 receptor in glaucoma" University of North Texas Health Science Center at Fort Worth; 2014.
Ponten et al. "In vivo pharmacology of the dopaminergic stabilizer pridopidine" European journal of pharmacology. Oct. 10, 2010;644(1-3):88-95.
Ponten et al. "The dopaminergic stabilizer pridopidine decreases expression of L-DOPA-induced locomotor sensitisation in the rat unilateral 6-OHDA model" European journal of pharmacology. Jan. 5, 2013;698(1-3):278-85.
Pozzo-Miller et al. "Rett Syndrome: Reaching for Clinical Trials" Neurotherapeutics. Jul. 2015;12(3):631.
Rabinovich-Guilatt et al. "The effect of mild and moderate renal impairment on the pharmacokinetics of pridopidine, a new drug for Huntington's disease" British journal of clinical pharmacology. Feb. 2016;81(2):246-55.
Rung et al. (2005). "The dopaminergic stabilizers (−)-OSU6162 and ACR16 reverse (+)-MK-801-induced social withdrawal in rats" *Progress in Neuro-Psychopharmacologyand Biological Psychiatry*, 29(5), 833-839.
Ryskamp et al. "The sigma-1 receptor mediates the beneficial effects of pridopidine ina mouse model of Huntington disease" Neurobiology of disease. Jan. 1, 2017; 97:46-59.
Sahlholm et al. "Pridopidine selectively occupies sigma-1 rather than dopamine D2 receptors at behaviorally active doses" Psychopharmacology. Sep. 2015;232(18):3443-53.
Sahlholm et al. "The dopamine stabilizers ACR16 and (−)-OSU6162 display nanomolar affinities at the σ-1 receptor" Molecular psychiatry. Jan. 2013;18(1):12-4.
Sandweiss et al. "Advances in understanding of Rett syndrome and MECP2 duplication syndrome: prospects for future therapies" The Lancet. Neurology. Aug. 2020;19(8):689-98.
Smith-Dijak et al. "Impairment and Restoration of Homeostatic Plasticity in Cultured Cortical Neurons From a Mouse Model of Huntington Disease" Frontiers in Cellular Neuroscience. 2019;13.
Squitieri et al. "Profile of pridopidine and its potential in the treatment of Huntington disease: the evidence to date" Drug Design, Development and Therapy. 2015;9:5827.
Sun et al. "The ups and downs of BDNF in Rett syndrome" Neuron. Feb. 2, 2006;49(3):321-3.
Supplementary European Search Report for European Application No. 17851614.2 dated Apr. 30, 2020.
Tedrof et al. (1999). "Long-lasting improvement following (−)-OSU6162 in a patient with Huntington's disease" *Neurology*, 53(7), 1605-1605.
Weng et al. "Rett syndrome: from bed to bench" Pediatrics and neonatology. Dec. 2011;52(6):309-16.
Xu et al. "EEA1 restores homeostatic synaptic plasticity in hippocampal neurons from Rett syndrome mice" The Journal of Physiology. Aug. 8, 2017;595(16):5699.
Yung-Chi et al. "Relationship between the inhibition constant (KI) and the concentration of inhibitor which causes 50 per cent inhibition (I50) of an enzymatic reaction" Biochemical pharmacology. Dec. 1, 1973;22(23):3099-108.
Zuccato et al. "Brain-derived neurotrophic factor in neurodegenerative diseases" Nature reviews. Neurology. Jun. 2009;5(6):311-22.

* cited by examiner

SEQUENCE LISTING

```
<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: 5' Primer Sequence

<400> SEQUENCE: 1

ggcacaatgc aggaaagg                                    18


<210> SEQ ID NO 2
<211> LENGTH: 21
<212> TYPE: DNA
<213> ORGANISM: Artificial Sequence
<220> FEATURE:
<223> OTHER INFORMATION: 3' Primer Sequence

<400> SEQUENCE: 2

tcagcaggca catagatagc c                                21
```

<210> SEQ ID NO 3
<211> LENGTH: 19
<212> TYPE: DNA
<213> ORGANISM: Artificial Sequence
<220> FEATURE:
<223> OTHER INFORMATION: 5' Primer Sequence

<400> SEQUENCE: 3
ttgtggccaa gcaggtact 19

<210> SEQ ID NO 4
<211> LENGTH: 20
<212> TYPE: DNA
<213> ORGANISM: Artificial Sequence
<220> FEATURE:
<223> OTHER INFORMATION: 3' Primer Sequence

<400> SEQUENCE: 4
gttgatgcct tcacagcgta 20

<210> SEQ ID NO 5
<211> LENGTH: 21
<212> TYPE: DNA
<213> ORGANISM: Artificial Sequence
<220> FEATURE:
<223> OTHER INFORMATION: 5' Primer Sequence

<400> SEQUENCE: 5
caatgtgtcc gtcgtggatc t 21

<210> SEQ ID NO 6
<211> LENGTH: 22
<212> TYPE: DNA
<213> ORGANISM: Artificial Sequence
<220> FEATURE:
<223> OTHER INFORMATION: 3' Primer Sequence

<400> SEQUENCE: 6
gtcctcagtg tagcccaaga tg 22

<210> SEQ ID NO 7
<211> LENGTH: 20
<212> TYPE: DNA
<213> ORGANISM: Artificial Sequence
<220> FEATURE:
<223> OTHER INFORMATION: 5' Primer Sequence

<400> SEQUENCE: 7
agtctccagg acagcaaagc 20

<210> SEQ ID NO 8
<211> LENGTH: 23
<212> TYPE: DNA
<213> ORGANISM: Artificial Sequence
<220> FEATURE:
<223> OTHER INFORMATION: 3' Primer Sequence

<400> SEQUENCE: 8
tgcaaccgaa gtatgaaata acc 23

<210> SEQ ID NO 9
<211> LENGTH: 22
<212> TYPE: DNA
<213> ORGANISM: Artificial Sequence
<220> FEATURE:
<223> OTHER INFORMATION: 5' Primer Sequence

<400> SEQUENCE: 9
gctgccttga tgtttacttt ga 22

<210> SEQ ID NO 10
<211> LENGTH: 23
<212> TYPE: DNA
<213> ORGANISM: Artificial Sequence
<220> FEATURE:
<223> OTHER INFORMATION: 3' Primer Sequence

<400> SEQUENCE: 10
aaggatggtc atcactcttc tca 23

<210> SEQ ID NO 11
<211> LENGTH: 19
<212> TYPE: DNA
<213> ORGANISM: Artificial Sequence
<220> FEATURE:
<223> OTHER INFORMATION: 5' Primer Sequence

<400> SEQUENCE: 11
ccgagagctt tgtgtggac 19

<210> SEQ ID NO 12
<211> LENGTH: 21
<212> TYPE: DNA
<213> ORGANISM: Artificial Sequence
<220> FEATURE:
<223> OTHER INFORMATION: 3' Primer Sequence

<400> SEQUENCE: 12
tcatgcaacc gaagtatgaa a 21

<210> SEQ ID NO 13
<211> LENGTH: 20
<212> TYPE: DNA
<213> ORGANISM: Artificial Sequence
<220> FEATURE:
<223> OTHER INFORMATION: 5' Primer Sequence

<400> SEQUENCE: 13
gcctttggag cctcctctac 20

<210> SEQ ID NO 14
<211> LENGTH: 19
<212> TYPE: DNA
<213> ORGANISM: Artificial Sequence
<220> FEATURE:
<223> OTHER INFORMATION: 3' Primer Sequence

<400> SEQUENCE: 14
gcggcatcca ggtaatttt 19

USE OF PRIDOPIDINE AND ANALOGS FOR TREATING RETT SYNDROME

CROSS-REFERENCE TO RELATED APPLICATIONS

This application is a National Phase Application of PCT International Application No. PCT/IL2021/051383, International Filing Date 19 Nov. 2021, which is a Continuation-in-Part of U.S. patent application Ser. No. 17/498,075, filed 11 Oct. 2021, and which is a Continuation-in-Part of U.S. patent application Ser. No. 16/952,123, filed 19 Nov. 2020, which are hereby incorporated by reference.

SEQUENCE LISTING STATEMENT

The ASCII file, entitled P-609324-PC-SQL-15SEP17.txt, created on Sep. 15, 2017, comprising 2,997 bytes, submitted concurrently with the filing of this application is incorporated herein by reference.

BACKGROUND

Rett Syndrome

Rett syndrome (RTT) is a neurodevelopmental disorder estimated to affect 1 in every 10,000 to live female births in all racial and ethnic groups. (Amaral 2007).

In 95%-97% of cases, RTT is caused by a mutation in the Methyl-CpG binding Protein 2 (MeCP2) gene located on the X chromosome. (Isaias 2014). The mutation is usually random and spontaneous. In less than 1% of recorded cases, the mutation is inherited or passed from one generation to the next. The MeCP2 gene is involved in the production of the methyl-cystine binding protein 2 (MeCP2) protein. The MeCP2 protein binds methylcytosine and 5-hydroxymethycytosine at CpG sites in promoter regions of target genes, controlling their transcription by recruiting co-repressors and co-activators. (Pozzo-Miller 2015).

In rare cases, RTT may also be caused by partial gene deletions or mutations in other genes such as cyclin-dependent kinase-like 5 (CDKL5), Forkhead box protein G1 (FOXG1), and possibly other genes that have not yet been identified.

RTT is an early-onset neurodevelopmental autism spectrum disorder that begins in infancy, and is divided into four stages. In the first stage, which occurs between the ages of 6 and 18 months, developmental maturation stalls after a period of seemingly normal development. In the second stage, between the ages of 1 and 4 years, a period of regression begins in which a child begins to lose acquired skills. At this stage, purposeful hand movements are replaced by stereotypical movements such as hand wringing or clapping, and social withdrawal begins, leading to the diagnosis of autism. At this stage gait disturbances become apparent, such as ataxia and apraxia.

Additional symptoms include respiratory dysrhythmias, sleep disturbances, bruxism, and spells of inappropriate laughing or crying.

The third stage, between the ages of 2 and 10, brings the deterioration to a plateau. Motor functions may stabilize and social interaction may improve, but these may be accompanied by seizures. At the fourth stage, from the age of 10 into adulthood, additional motor deterioration occurs. Patients often develop parkinsonism (rigidity, bradykinesia and tremor), as well as muscle weakness and osteoperosis (Sandweiss 2020).

RTT patients demonstrate abnormal neuronal morphology, and decreased brain size, which manifests with incoordination, intellectual decline, gait abnormalities, and seizures. (Weng 2011). Currently, there is no treatment for RTT, only supportive care.

Pridopidine

Pridopidine (4-[3-(methylsulfonyl)phenyl]-1-propyl-piperidine) (formerly known as ACR16) is a drug under development for treatment of Huntington disease. The chemical name of pridopidine is 4-(3-(Methylsulfonyl)phenyl)-1-propylpiperidine and its Chemical Registry Number is CAS 346688-38-8 (CSID:7971505 2016). The Chemical Registry number of pridopidine hydrochloride is 882737-42-0 (CSID:25948790 2016).

Pridopidine selectively binds the sigma-1 receptor (S1R, Ki=0.057 μM) with high affinity. It binds with low affinity to additional receptors in the central nervous system, including the dopamine D2/D3 receptors, adrenergic α2C receptor, serotonin 5-HT1A. Pridopidine has ~28×-fold higher selectivity for the S1R compared to adrenergic α2C and dopamine D3 receptors (Ki=1.28 and 1.63 μM, respectively), ~64-fold higher selectivity for the 5-HT 1A receptor (Ki=3.63 μM), ~100-fold higher selectivity for the sigma-2 receptor (S2R, Ki=5.45 μM) and ~500-fold higher selectivity compared to the dopamine D2 receptor (Ki=29.5 μM) (Table 1) (Johnston et al, 2019).

TABLE 1

Pridopidine Binding Affinity and Selectivity to CNS Receptors

| Target Receptor | Binding Ki (μM) | Fold Selectivity for S1R |
|---|---|---|
| Sigma-1 (σ1R) | 0.057 | 1 |
| Adrenergic α2C | 1.28 | 28 |
| Dopamine D3 | 1.63 | 28.5 |
| Serotonin 5-HT1A | 3.63 | 64 |
| Sigma-2 (σ2R) | 5.45 | 96 |
| Dopamine D2 | 29.5 | 517.5 |

Source: Johnston et al., 2019

The S1R is an endoplasmic reticulum (ER) protein implicated in cellular differentiation, neuroplasticity, neuroprotection and cognitive function in the brain. Activation of the S1R by pridopidine leads to upregulation of pathways known to promote neuronal plasticity and survival. Pridopidine upregulates the secretion and downstream signaling of the neuroprotective brain-derived neuroptrophic factor (BDNF) (Geva et al., 2016).

A decrease in BDNF is associated with Rett pathogenesis. Homeostatic synaptic plasticity (HSP), the processes that maintain the stability of neuronal networks and underlie learning and cognitive capabilities, are regulated by BDNF (Smith-Dijak et al., 2019). HSP is also disrupted in Rett syndrome. Mecp2-deficient neurons show impaired homeostatic synaptic plasticity (Xin xu and Pozzo-Miller, J physiolo 2017). Pridopidine restores impaired HSP in cultured cortical neurons from the HD YAC128 mouse model (Smith-Dijak et al., 2019).

Modulation of the BDNF pathway is a major component of pridopidine's S1R-mediated neuroprotective effects.

SUMMARY OF THE INVENTION

This invention provides a method for treating a subject afflicted with Rett syndrome (RTT) comprising administering to the subject a pharmaceutical composition comprising pridopidine or a pharmaceutically acceptable salt thereof and at least one of compounds 1-8:

(Compound 1)

(Compound 2)

(Compound 3)

(Compound 4)

(Compound 5)

(Compound 6)

-continued (Compound 7)

or (Compound 8)

or a pharmaceutically acceptable salt thereof, so as to thereby treat the subject.

This invention also provides a method for increasing brain-derived neurotrophic factor (BDNF) levels in a subject afflicted with RTT comprising administering to the subject a pharmaceutical composition comprising pridopidine or a pharmaceutically acceptable salt thereof and at least one of compounds 1-8, or a pharmaceutically acceptable salt thereof so as to thereby increase BDNF serum level in the subject.

Left: "the cloud graph": Visualization of the control–disease–(disease+treatment) groups relationship in the optimal discrimination feature space. The clouds are plotted in the two-dimensional space, the two coordinates being the highest ranked de-correlated features analyzed by the automated NeuroCube system (more information about Neurocube can be found in Example 1 and Example 3).

The drug treatment effect can be represented as a combination of two components: one along the direction of the "recovery line" (the line connecting the centers of the control (WT) and disease (MECP2-KO) clouds, shown as a thick arrow to the left with diagonal lines on top), and the component orthogonal to ("pointing away" from) that direction shown as an arrow pointing up with parallel lines within. The relative length of the "recovery" arrow with respect to the control-disease distance can then be interpreted as the "recovery due to the drug", whereas the relative length of the "other effect" (orthogonal with parallel lines inside) arrow represents feature changes that move the disease mice+treatment group away from the control group. The summary of this analysis can be effectively represented as a bar graph (right pane in FIG. 1A) which is typically referred to as the recovery signature.

Right: "the recovery signature" graph: The bar graph represents the summary of the recovery analysis. The overlap and discrimination probability sum up to 100%. The recovery ranges from 0 to the discrimination probability value. The lower the overlap, the better the quality of the disease model, and the higher the discrimination power between the WT and Rett mice groups. The "other behavioral effect" is in the same relative units (relative to the length of the distance between the WT and Rett mice groups).

Figure 2:
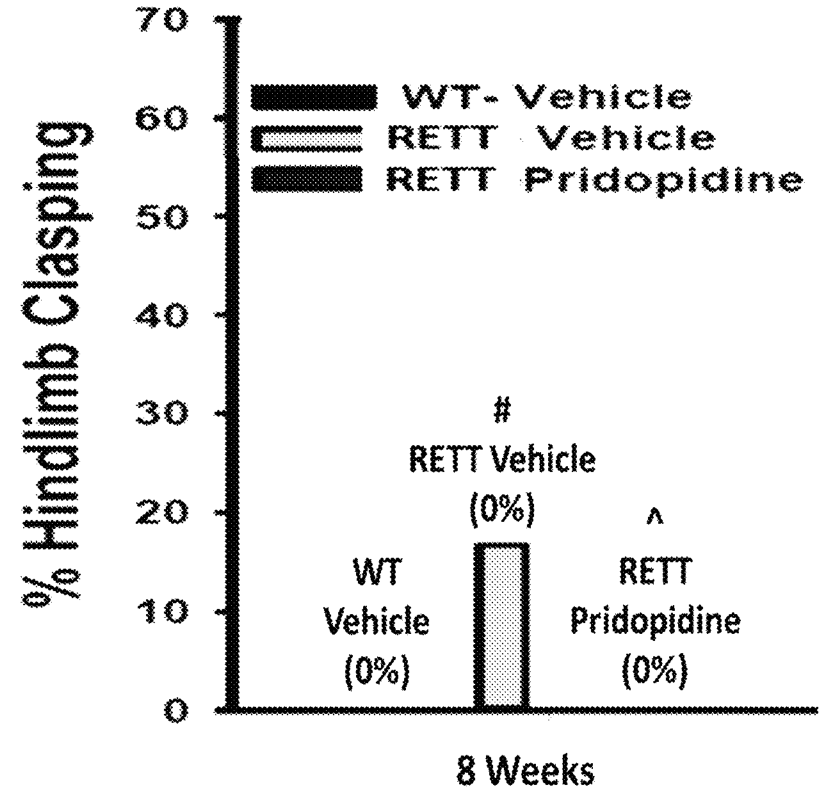

FIG. 2: Pridopidine rescues hindlimb clasping phenotype in Rett model mice at 8 weeks of age. Clasping is used to assess muscular strength in limb muscles. Hindlimb clasping is measured in mice held by the tail and gently lifted until the front paws just lift off the counter surface. The experimenter observes the legs and determines clasping or splaying of limbs. Wild-type (WT, n=24) mice show no clasping at 8 weeks of age (0%). Rett mice (female MECP2 heterozygous, "RETT" mice, n=20) show significant clasping (~17%) at 8 weeks of age (#p<0.05 vs. placebo). Rett mice ("RETT") treated with pridopidine (30 mg/kg bid, n=20) show rescue (i.e. no clasping, 0%) at 8 weeks, ^p<0.06 compared to RETT-vehicle group. Data are mean±SEM, N-1 two-proportional tests. Source: DPR-2016-061

Figure 3:
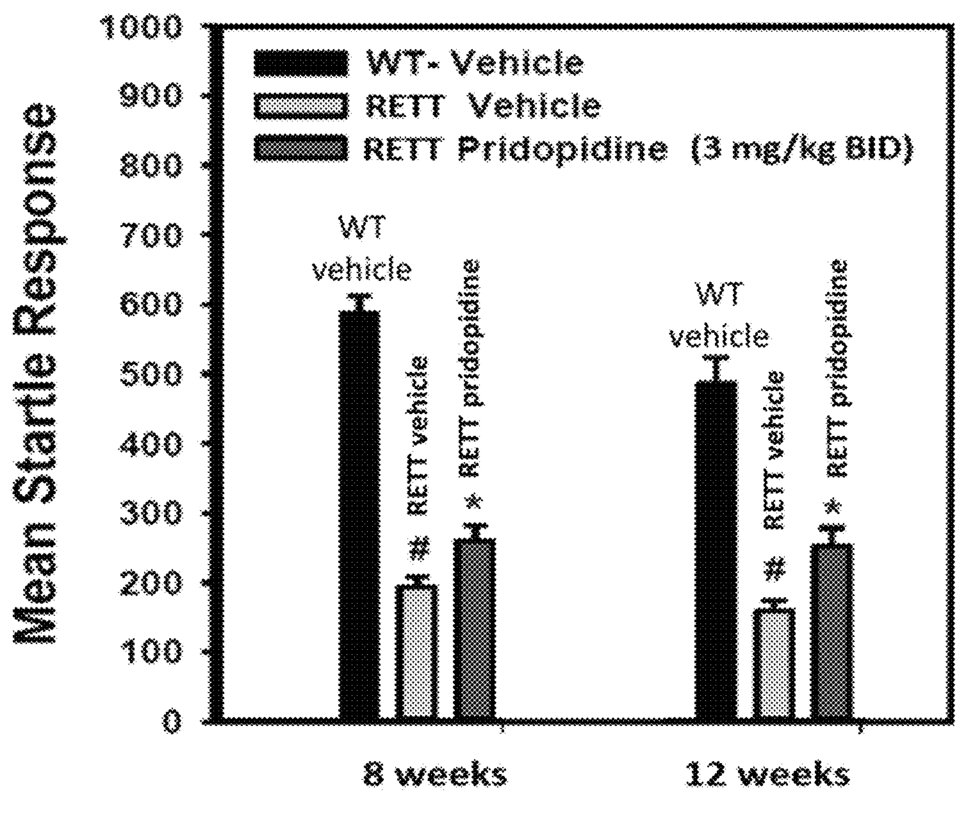

FIG. 3: Pridopidine improves mean startle response in response to acoustic stimuli in RETT mice at 8 and 12 weeks of age. The acoustic startle measures an unconditioned reflex response to external auditory stimulation. Prepulse inhibition (PPI) consists of an inhibited startle response to an auditory stimulation following the presentation of a weak auditory stimulus or prepulse. The acoustic startle is measured by placing mice in a sound-attenuated startle chamber which measures the force of the movements made by the mouse. The amount of inhibition following an acoustic prepulse is expressed as a percentage of the basic startle response (from startle alone trials), excluding the startle response of the first habituation block. Vehicle-treated RETT mice (n=20) show a significant inhibition in startle response compared to WT mice (n=24), by ~65% and ~75% at 8 and 12 weeks, respectively (p<0.05). Pridopidine has a significant rescue effect, of ~40% and ~50% at 8 and 12 weeks, respectively (n=24, p<0.05) Data are expressed as mean±SEM. #p<0.05 compared to WT-vehicle group. *p<0.05 compared to Rett-vehicle group FIG. 4: Pridopidine recovers gait features in female Rett model mice at 8 weeks of age. Summary of recovery analysis of gait features in female Rett model mice by Pridopidine (30 mg/kg twice daily (bid)) at 8 weeks of age. Untreated Rett mice (lower right-most cloud) can be discriminated from WT mice (upper cloud), by gait features, as the two clouds are completely separated. The bar graphs show pridopidine 30 mg/kg bid significantly improves gait in Rett mice by 45% (p=0.0181) (darkest color) at 8 weeks. The cloud graphs are used to visualize WT Rett female mice (lower right-most cloud), and Rett female mice+pridopidine (lower-left most cloud) relationship in the optimal discrimination feature space (see explanation in FIG. 1).

Figure 5:
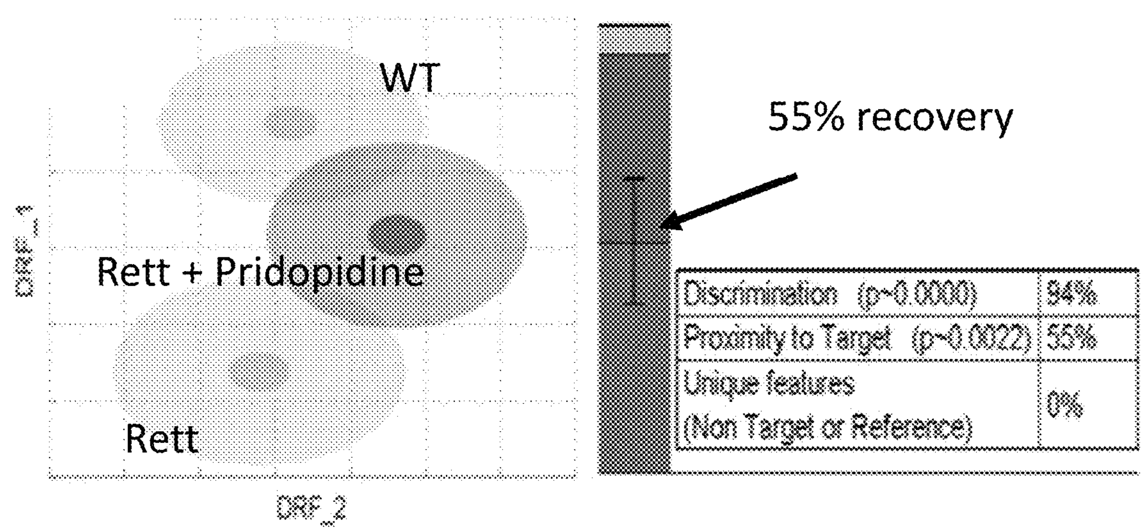

FIG. 5: Pridopidine recovers gait features in female Rett model mice at 12 weeks of age. Summary of recovery analysis of gait features in Rett female mice by Pridopidine (30 mg/kg bid) at 12 weeks of age. Untreated Rett mice (lower left-most cloud) can be discriminated from WT mice (upper cloud), by gait features, as the two clouds are completely separated. Pridopidine (30 mg/kg bid) shows significant recovery in gait features of Rett mice by 55% (p=0.0022) (darkest color) at 12 weeks. The cloud graphs are used to visualize WT (upper cloud), Rett mice (lower left-most cloud), and Rett+pridopidine (lower-right most cloud) relationship in the optimal discrimination feature space (see explanation in FIG. 1).

FIGS. 6A-6C, 7, 8, 9, 10: These figures display mRNA levels of BDNF transcripts measured in the brains of female heterozygous MeCP2 (Rett) mice. Column A represents vehicle treated WT mice, column B represents vehicle treated Rett female mice, column C represents pridopidine treated Rett female mice (3 mg/kg bid) and column D represents pridopidine treated Rett female mice (30 mg/kg bid). The relative quantity of the gene target is normalized to the geometric means of the relative quantity of the housekeeping genes APT5B, GAPDH and RPK12A. Relative level of the target gene was then normalized to the WT vehicle group. All data are represented as the mean±SEM. ANOVA followed by Tukey's multiple comparisons test.

Figure 6A:
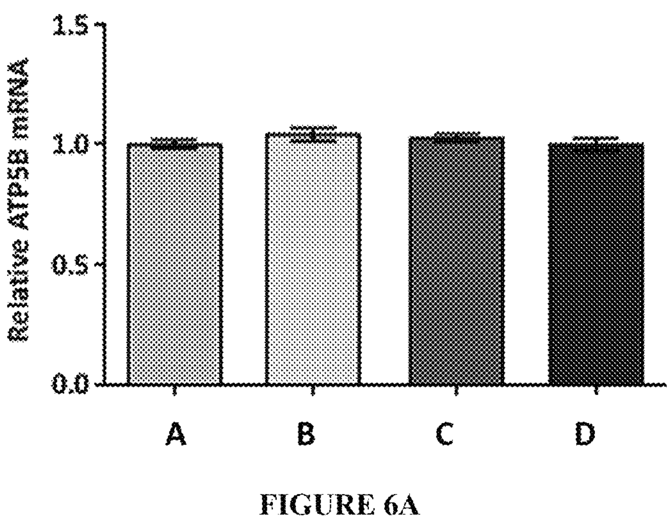
Figure 6B:
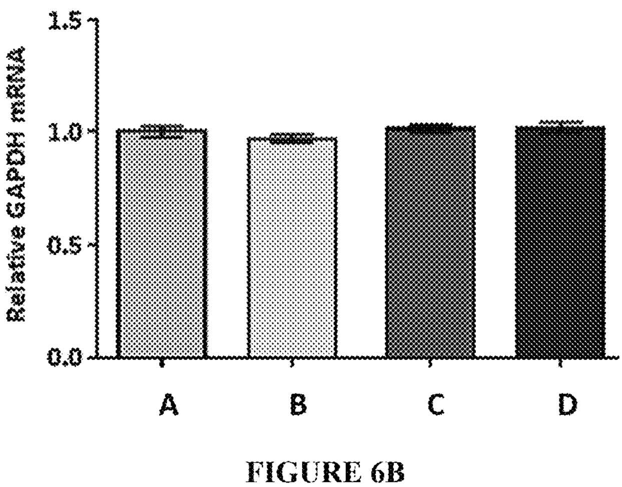
Figure 6C:
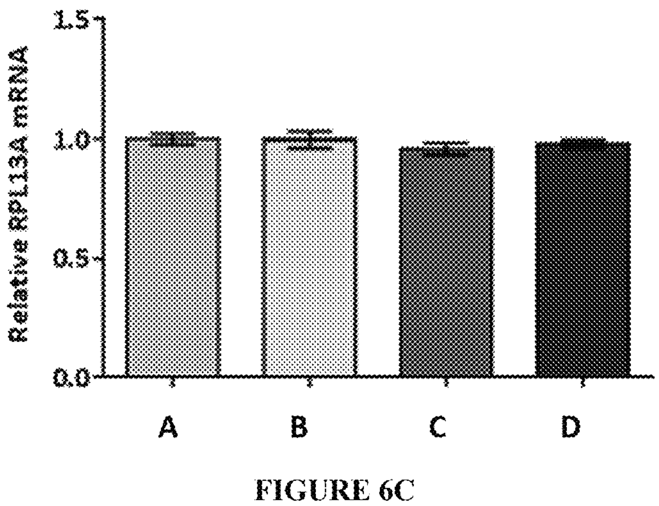

FIGS. 6A-6C: Pridopidine does not affect levels of housekeeping genes ATP5B. GAPDH, and RPL13A. Relative mRNA expression of whole brain control housekeeping genes: ATP5B (6A), GAPDH (6B) and RPL13A (6C); each normalized to the geometric means of the other two genes. Pridopidine does not affect the expression of control housekeeping genes.

Figure 7:
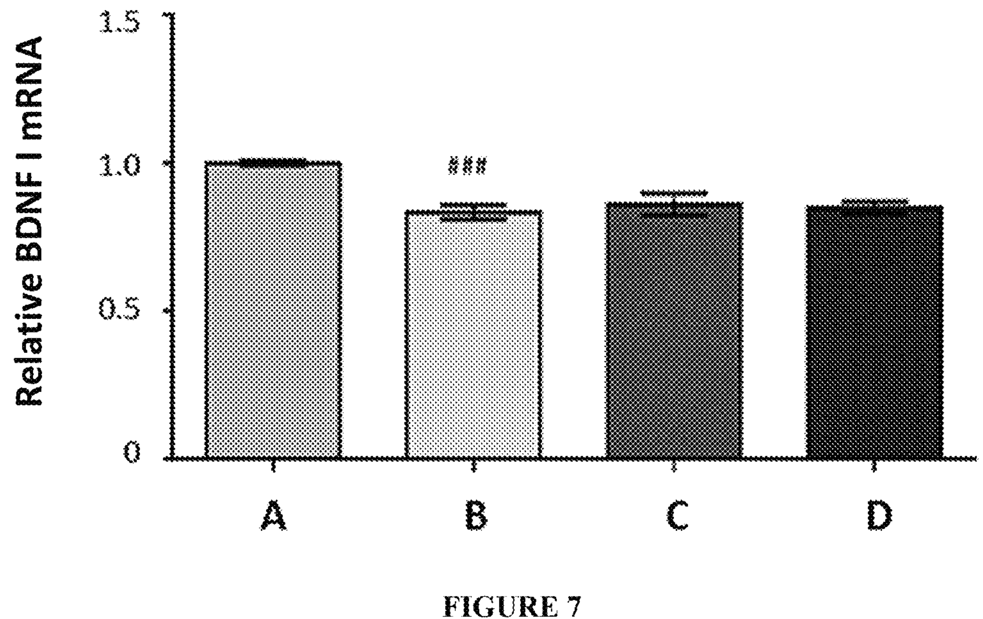

FIG. 7: Pridopidine has no effect on BDNF I mRNA levels. Relative mRNA expression of BDNF I in whole brain. In Rett mice, BDNF I levels are reduced by ~20% (p<0.001). Pridopidine does not affect BDNF I levels in Rett mice.

Figure 8:
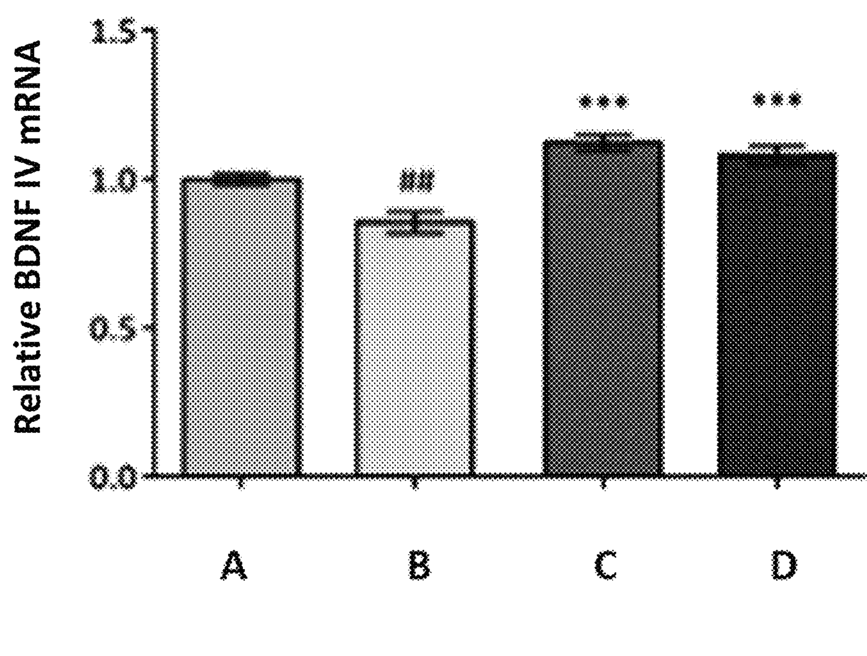

FIG. 8: Pridopidine rescues BDNF IV mRNA levels Relative mRNA expression of BDNF IV in whole brain. In Rett mice, BDNF IV levels are reduced by ~15% (p<0.001). Pridopidine significantly increases the mRNA levels of BDNF IV by ~30% at 3 mg/kg bid and 30 mg/kg bid doses (p<0.001).

Figure 9:
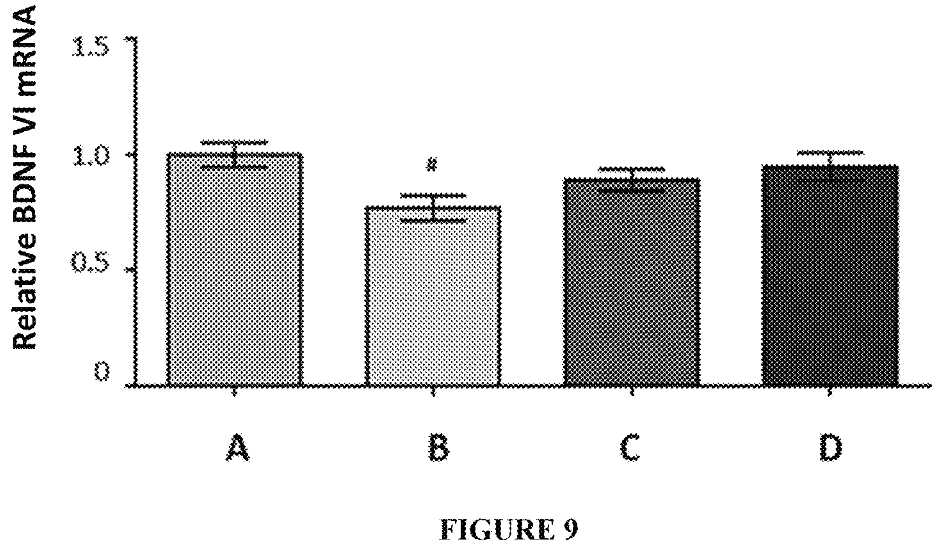

FIG. 9: Pridopidine has no effect on BDNF VI mRNA levels. Relative mRNA expression of BDNF VI in whole brain. In Rett mice, BDNF I levels are reduced by ~25% (p<0.05). Pridopidine does not affect BDNF VI levels in Rett mice.

Figure 10:
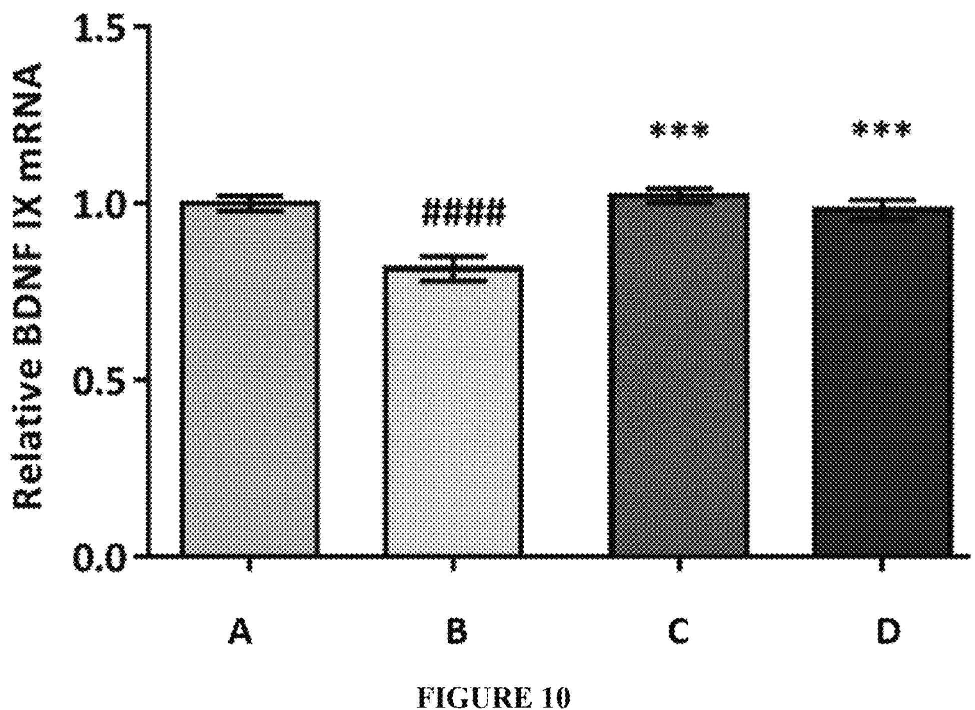

FIG. 10: Pridopidine rescues BDNF IV mRNA levels Relative mRNA expression of BDNF IV in whole brain. In Rett mice, BDNF IV levels are reduced by ~15% (p<0.0001). Pridopidine significantly increases the mRNA levels of BDNF IV back to WT levels at 3 mg/kg bid and 30 mg/kg bid doses (p<0.001).

Figure 11A:
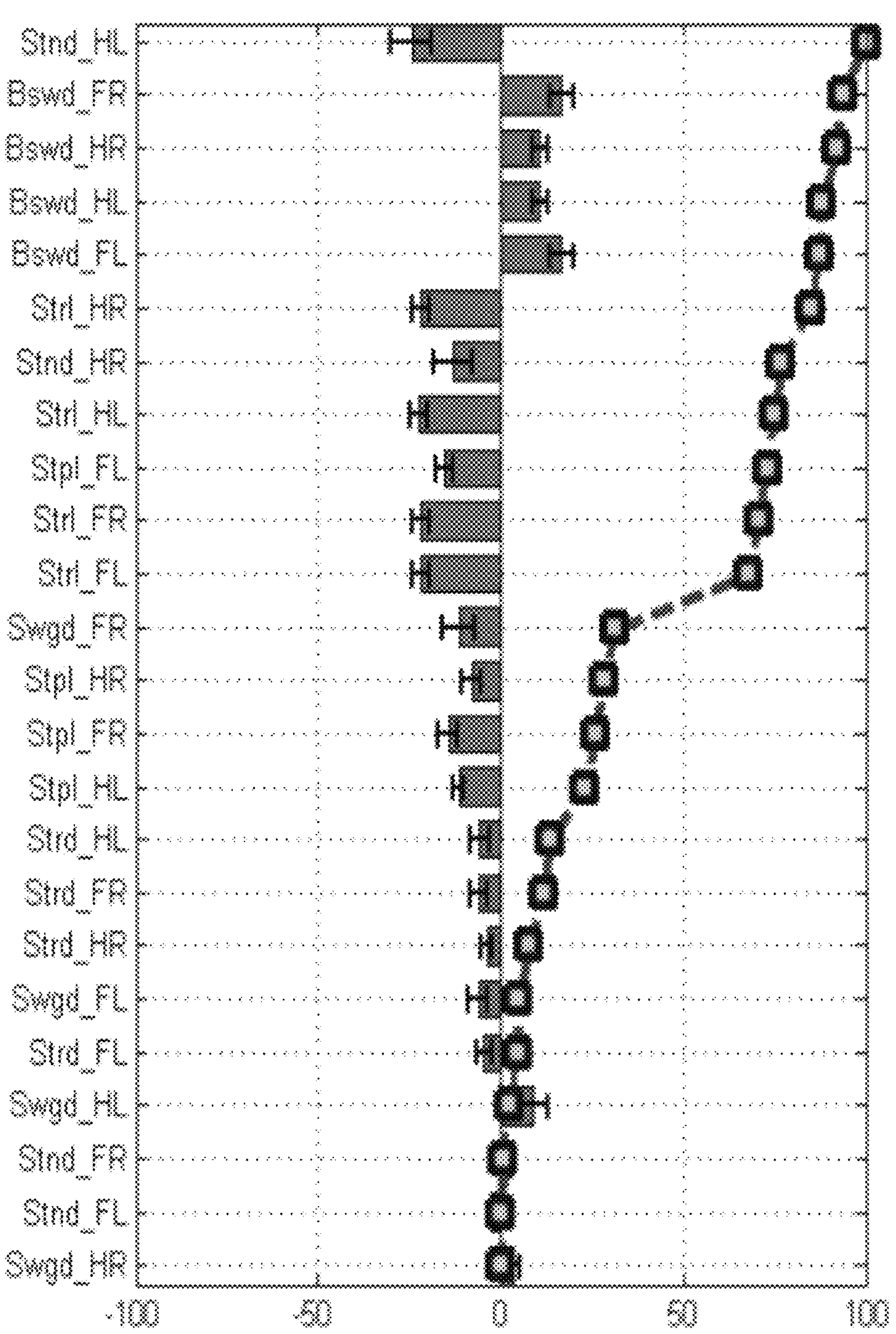
Figure 11B:
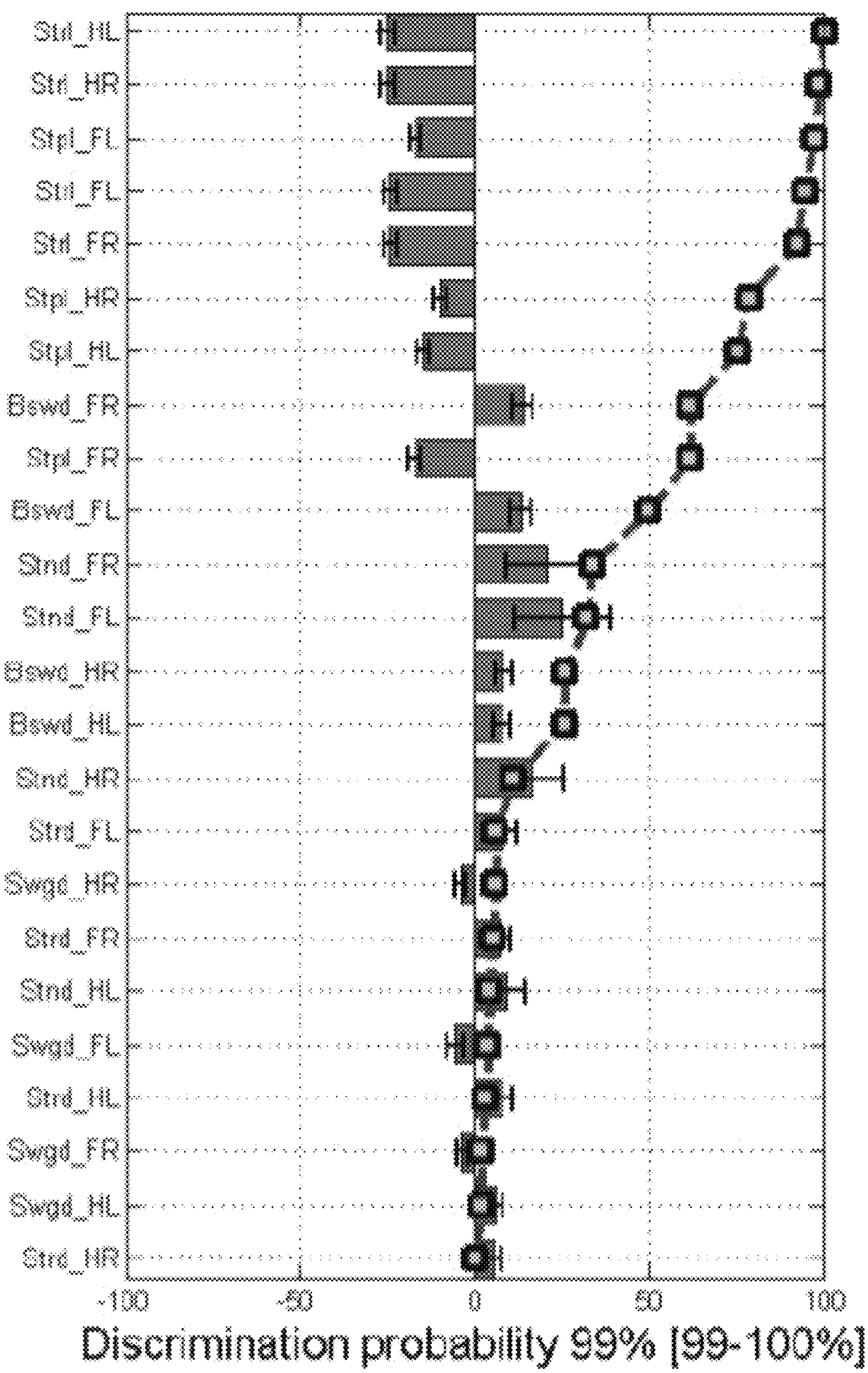

FIGS. 11A-11B: Feature discrimination in gait analysis by Neurocube

In these experiments B6.129P2-Mecp2tm2Bird/J (Rett-KO) male mice were used. This figure displays the discrimination plots which are the output of gait analysis by Neurocube, the automated tool used for evaluating pridopidine's effects. The columns represent the different behavioral features assessed by NeuroCube together with their values. The curve with the square outlines shows the ranking of each of the behavioral features. Ranking relates to the ability of a specific feature to discriminate between the control and disease groups. Relative difference (%) between feature values in two different sets is calculated and plotted in the order corresponding to feature ranks together with their ranks varying from 0 to 100%. Feature name is a combination of the parameter name and the paw name: STRL: stride length; STPL: step length, BSWD: base width, STRD: stride duration, STND: stand duration, SWGD: swing duration, Avg_speed: average speed of the run, FR—forelimb, right, FL—forelimb, left, HR—hindlimb, right, HL—hindlimb, left.

Features are arranged in the figure from top to bottom based on their rank. More information on Neurocube can be found in Example 1 and Example 3. Discrimination plots of Rett-KO male mice compared to WT mice at 6 (A) and 7 (B) weeks of age.

Figure 12:
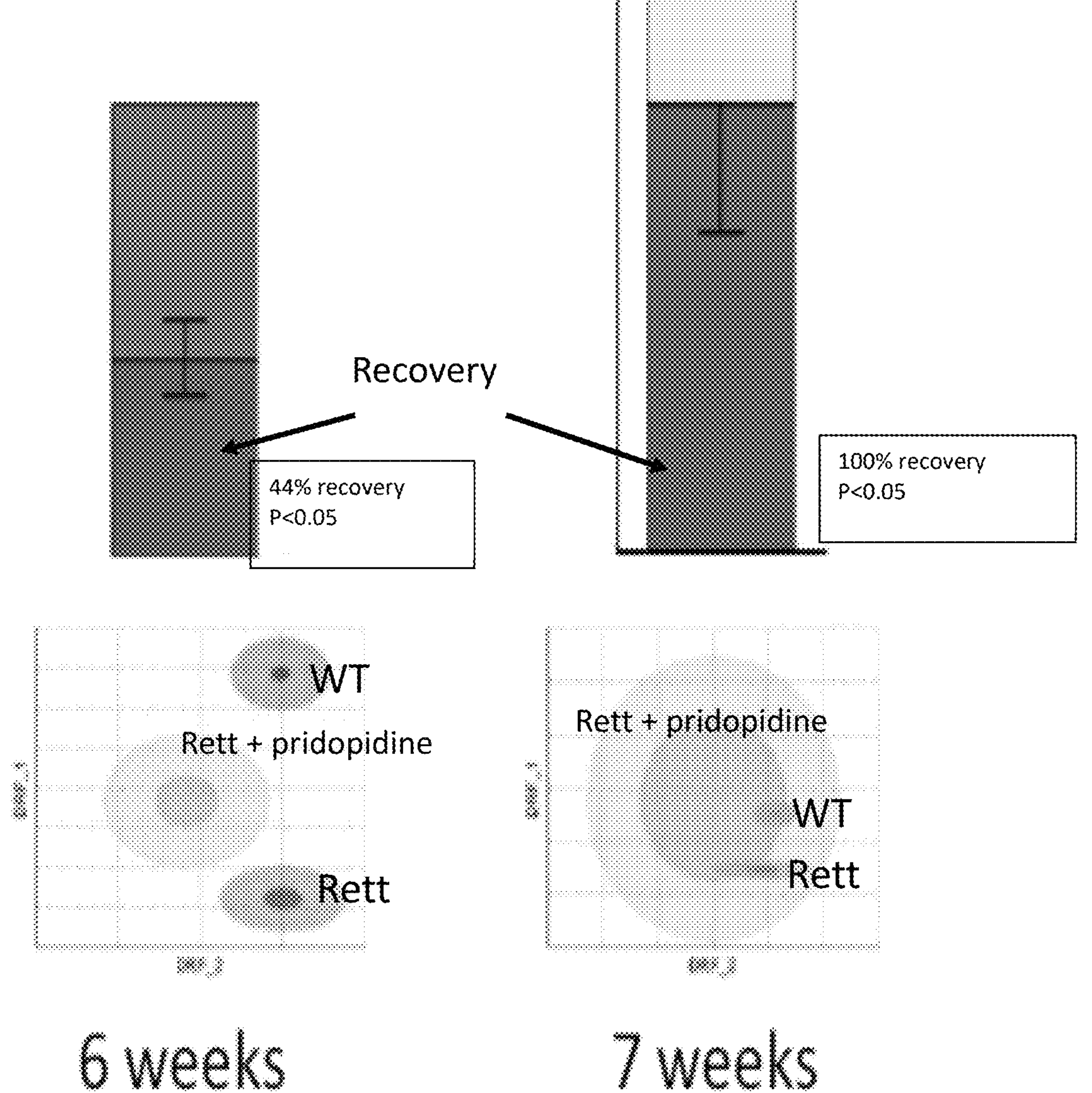

FIG. 12: Pridopidine recovers gait features in male Rett mice at 6 and 7 weeks of age. Summary of recovery analysis from Rett syndrome effects in B6.129P2-Mecp2tm2Bird/J (Rett-KO) male mice (see explanation in FIG. 1). Top: bar graph showing the recovery effects of Pridopidine (30 mg/kg bid) in Rett-KO model mice. Bottom: The cloud graph to visualize WT, Rett, and Rett+pridopidine relationship in the optimal discrimination feature space (WT, Rett, Rett+pridopidine). Pridopidine exhibits 44% (left, $p<0.05$) and 100% (right, $p<0.05$) recovery of gait deficits in Rett model mice at 6 and 7 weeks of age, respectively. One-way ANOVA.

Figure 13A:
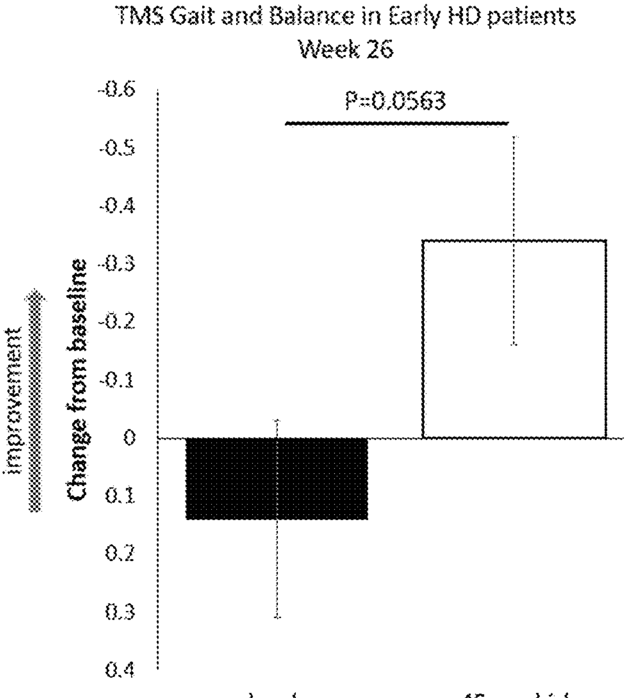
Figure 13B:
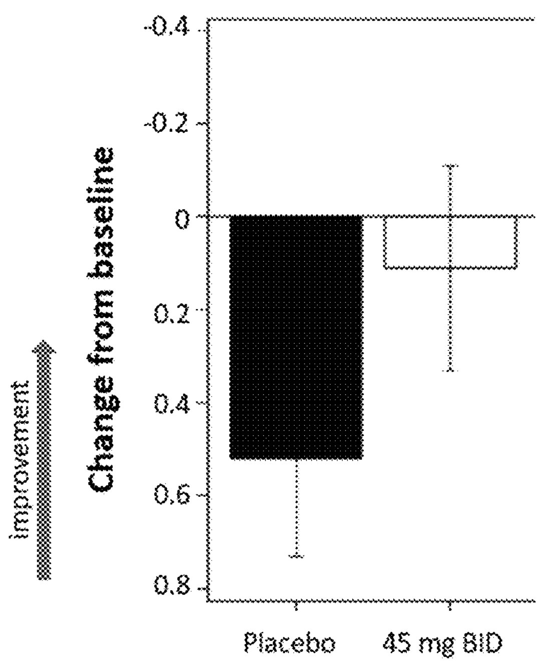

FIGS. 13A-13B: Pridopidine 45 mg bid improves gait and balance in early HD (TFC 7-13) patients at 26 and 52 weeks. Change from baseline in UHDRS TMS gait balances week 26 (A) and Week 52(B) in early HD (baseline TFC 7-13) patients in the PRIDE-HD study. Patients on placebo demonstrate a worsening in gait and balance (Δ from baseline 0.14, positive value indicates worsening). Pridopidine efficacy was assessed throughout the 52-week period using Mixed Models Repeated Measures (MMRM) analyses of change from baseline in the Unified Huntington's Disease Rating Scale Total Motor Score gait and balance (UHDRS TMS; gait and balance).

At week 26, pridopidine 45 mg bid improves gait function vs placebo (A from placebo −0.48, negative values indicate improvement, p=0.0563). Table 2, below, accompanies the figure. At week 52 Pridopidine 45 mg bid treatment shows a trend towards improvement compared to placebo (Δ from placebo −0.41, negative values indicate an improvement).

TABLE 2

Pridopidine 45 mg bid improves gait and balance in early HD patients (HD1 + HD2, TFC 7-13) at 26 and 52 weeks in PRIDE–HD

| | Placebo | Pridopidine 45 mg bid |
|---|---|---|
| | Week 26 | |
| N | 62 | 59 |
| from baseline (SE)Δ | 0.14 (0.17) | −0.34 (0.18) |
| from placeboΔ | | −0.48 |
| p-value | | 0.0563 |
| | Week 52 | |
| N | 62 | 59 |
| Δ from baseline (SE) | 0.52 (0.21) | 0.11 (0.22) |
| Δ from placebo | | −0.41 |
| p-value | | 0.18 |

Figure 14A:
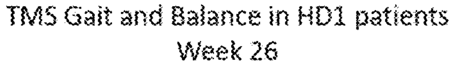
Figure 14A:
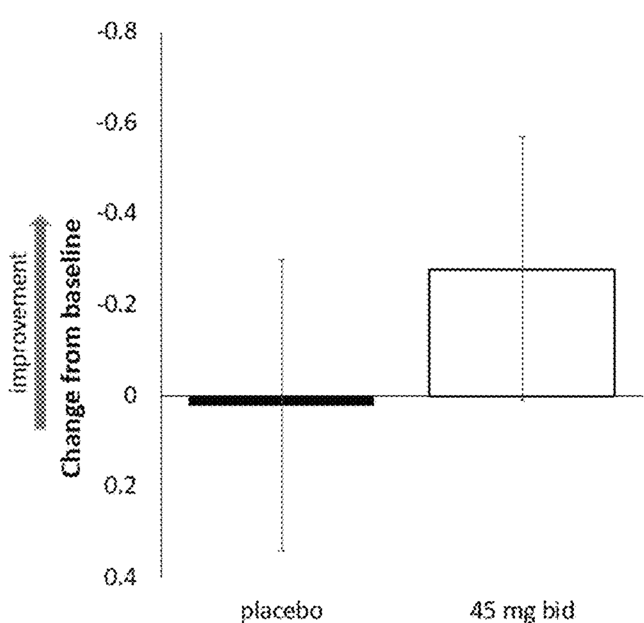
Figure 14B:
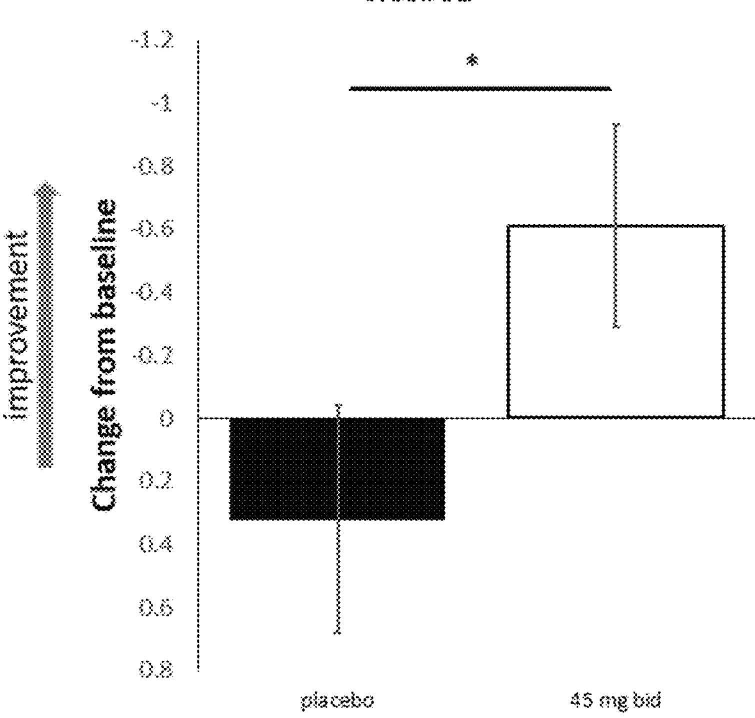

FIG. 14A-14B: Pridopidine 45 mg bid improves gait and balance in HD1 (TFC 11-13) patients at 26 and 52 weeks Change from baseline in UHDRS TMS gait balances at week 26 (A) and at week 52 (B) in HD1 (baseline TFC 11-13) patients in the PRIDE-HD study. Pridopidine efficacy was assessed throughout the 52-week period using Mixed Models Repeated Measures (MMRM) analyses of change from baseline in the Unified Huntington's Disease Rating Scale Total Motor Score gait and balance (UHDRS TMS; gait and balance).

At week 26, patients receiving placebo demonstrate worsening in gait and balance. Pridopidine shows a trend towards improvement (Δ from placebo −0.31) Table 3, below, accompanies the figure. At week 52, patients on placebo demonstrate worsening from baseline. Pridopidine 45 mg bid treatment shows a significant improvement compared to placebo (Δ from placebo −0.94, p=0.0445, negative values indicate an improvement).

TABLE 3

Pridopidine 45 mg bid improves gait and balance in HD1 (TFC 11-13) patients at 26 and 52 weeks in PRIDE–HD

| | Placebo | Pridopidine 45 mg bid |
|---|---|---|
| | Week 26 | |
| N | 12 | 17 |
| Δ from baseline (SE) | 0.02 (0.32) | −0.29 (0.28) |
| Δ from placebo | | −0.31 |
| p-value | | 0.4459 |
| | Week 52 | |
| N | 12 | 17 |
| Δ from baseline (SE) | 0.32 (0.36) | −0.61 (0.32) |
| Δ from placebo | | −0.94 |
| p-value | | 0.0445 |

Figure 15A:
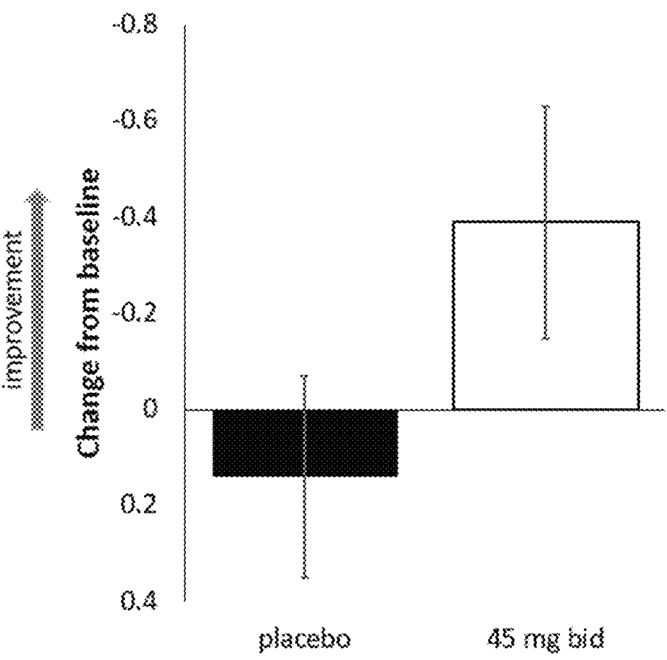
Figure 15B:
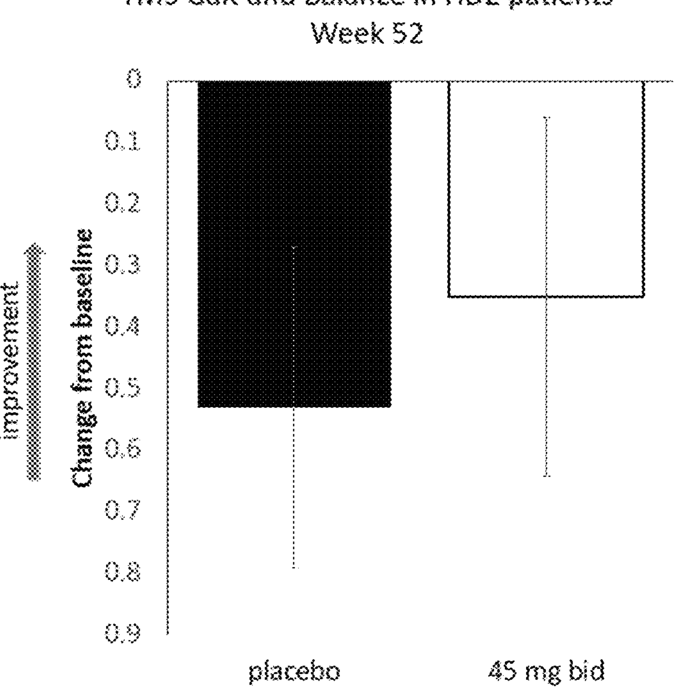

FIG. 15A-15B: Pridopidine 45 mg bid improves gait and balance in HD2 (TFC 7-10) patients at 26 and 52 weeks Change from baseline in UHDRS TMS gait balances at week 26 (A) and week 52 (B) in HD2 (baseline TFC 7-10) patients in the PRIDE-HD study. Pridopidine efficacy was assessed throughout the 52-week period using Mixed Models Repeated Measures (MMRM) analyses of change from baseline in the Unified Huntington's Disease Rating Scale Total Motor Score gait and balance (UHDRS TMS; gait and balance). At both 26 weeks and 52 weeks, pridopidine 45 mg bid treatment shows a trend towards improvement compared to placebo (Δ from placebo is −0.53 and −0.18 for weeks 26 and 52, respectively; negative values indicate an improvement). Table 4, below, accompanies the figure.

TABLE 4

Pridopidine 45 mg bid improves gait and balance in HD2 patients (TFC 7-10) at 26 and 52 weeks in PRIDE–HD

| | Placebo | Pridopidine 45 mg bid |
|---|---|---|
| | Week 26 | |
| N | 50 | 42 |
| Δ from baseline (SE) | 0.14 (0.21) | −0.39 (0.24) |
| Δ from placebo | | −0.53 |
| p-value | | 0.0936 |
| | Week 52 | |
| N | 50 | 42 |
| Δ from baseline (SE) | 0.53 (0.26) | 0.35 (0.29) |
| Δ from placebo | | −0.18 |
| p-value | | 0.6352 |

Figures 16A, 16B:
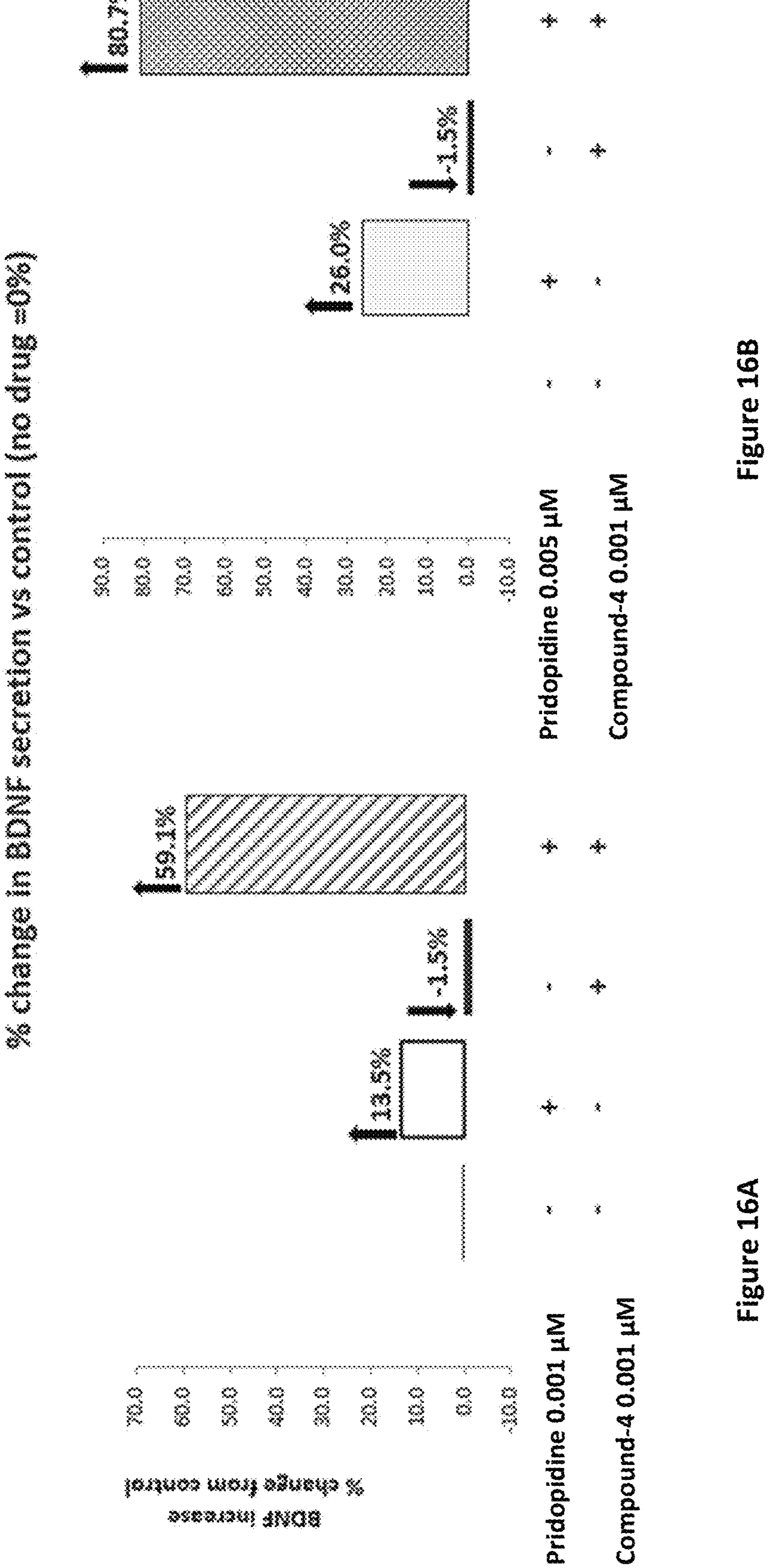

FIGS. 16A-16B: Pridopidine and Compound 4 have a synergistic effect on BDNF release in B104 rat neuroblastoma cells. B104 neuroblastoma cells were incubated for 5 days with test compounds, and BDNF levels were assessed using in-situ ELISA. FIG. 16A: Pridopidine at a concentration of 0.001 μM and Compound 4 at a concentration of 0.001 μM. Pridopidine alone increases BDNF secretion by 13.5%. Compound 4 alone had no effect on BDNF secretion—(1.5%). Pridopidine and compound 4 together increase BDNF secretion by 59.1%, an effect which is greater than the added effect of both compounds administered on their own. FIG. 16B: Pridopidine at a concentration of 0.005 μM and Compound 4 at a concentration of 0.001 μM. Pridopidine alone increases BDNF secretion by 26.0%. Compound 4 alone had no effect on BDNF secretion (−1.5%). Pridopidine and compound 4 together increase BDNF secretion by 80.7%, an effect which is greater than the added effect of both compounds administered on their own.

Figure 17:
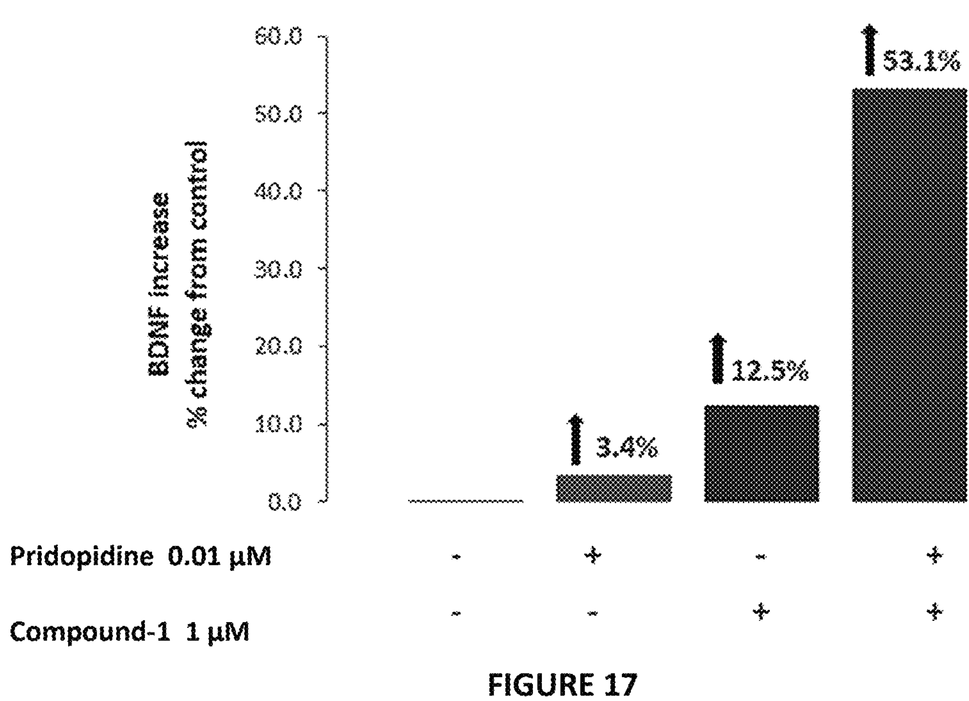

FIG. 17: Pridopidine and Compound 1 have a synergistic effect on BDNF release in B104 cells. Synergistic effect of pridopidine and Compound 1 on BDNF Release from B104 cells. B104 neuroblastoma cells were incubated for 5 days with test compounds, and BDNF levels were assessed using in-situ ELISA. Pridopidine at a concentration of 0.011 μM alone increases BDNF secretion by 3.4%. Compound 1 at a concentration of 1 μM alone increases BDNF secretion by 12.5%. Pridopidine and compound 1 together increase BDNF secretion by 53.1%, an effect which is greater than the added effect of both compounds administered on their own.

DETAILED DESCRIPTION OF THE INVENTION

This invention provides a method for treating a subject afflicted with Rett syndrome (RTT) comprising administering to the subject a pharmaceutical composition comprising pridopidine or a pharmaceutical acceptable salt thereof so as to thereby treat the subject.

This invention provides a method for treating a subject afflicted with Rett syndrome (RTT) comprising administering to the subject a pharmaceutical composition comprising pridopidine or a pharmaceutical acceptable salt thereof and at least one of compounds 1-8:

(Compound 1)

$SO_2CH_3$ OH N , (Compound 2)

$SO_2CH_3$ N $SO_2CH_3$ $SO_2CH_3$, (Compound 3)

$O_2S$ $SO_2$ N Pr N Pr,

-continued (Compound 4)

$SO_2CH_3$ OH N , (Compound 5)

$SO_2CH_3$ $O^-$ $N^+$ , (Compound 6)

$SO_2CH_3$ N , (Compound 7)

$SOCH_3$ N , or (Compound 8)

$SO_2CH_3$ N .

So as to thereby treat the subject.

In one embodiment, this invention provides a method for delaying the onset, preventing worsening, delaying worsening, or improving at least one symptom associated with Rett syndrome in a subject afflicted with Rett syndrome, wherein the method comprises administering a pharmaceutical composition comprising pridopidine or a pharmaceutically acceptable salt thereof and at least one of compounds 1-8, or a pharmaceutically acceptable salt thereof.

In one embodiment, the subject is a human patient. In one embodiment, the human patient is female.

In another embodiment, the human patient is male.

In one embodiment, the subject has a mutation in the methyl CpG binding protein 2 (MECP2) gene.

In one embodiment, the subject has a mutation in the cyclin-dependent kinase-like 5 (CDKL5) gene.

In one embodiment, subject has a mutation in the Forkhead box protein G1 (FOXG1) gene.

In some embodiments, the method of this invention comprises administering a pharmaceutical composition comprising pridopidine or pharmaceutically acceptable salt thereof and at least one of Compounds 1-8 or pharmaceutically acceptable salt thereof. In other embodiments, the pridopidine salt is pridopidine hydrochloride. In another embodiment, the pridopidine is hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, the naphthalene-2-sulphonate, phthalate, salicylate, sorbate, stearate, succinate, tartrate or toluene-p-sulphonate salt. In some embodiments, the method of this invention comprises administering a pharmaceutical composition comprising pridopidine or pharmaceutically acceptable salt thereof and at least one of compounds 1-8 or pharmaceutically acceptable salt thereof. In other embodiment, the at least one of compounds 1-8 salt is a hydrochloride salt. In another embodiment, the at least one of compounds 1-8 salt is a hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, the naphthalene-2-sulphonate, phthalate, salicylate, sorbate, stearate, succinate, tartrate or toluene-p-sulphonate salt.

In one embodiment, the pharmaceutical composition disclosed herein is administered orally, nasally, inhaled, by subcutaneous injection, or through an intravenous, intraperitoneal, intramuscular, intranasal, buccal, vaginal, rectal, intraocular, intrathecal, topical or intradermal route. In one embodiment, the pridopidine is administered orally.

In one embodiment, the pharmaceutical composition disclosed herein is administered in the form of an aerosol, an inhalable powder, an injectable, a liquid, a gel, a solid, a capsule, a tablet or multiparticulates In one embodiment, the pharmaceutical composition disclosed herein is administered orally and formulated as a tablet, a capsule, a pill, a powder, multiparticules in capsule or sachet, liquid solution or as a liquid suspension.

In one embodiment, the pharmaceutical composition disclosed herein is administered periodically.

In one embodiment, the pharmaceutical composition disclosed herein is administered less often than once daily. In one embodiment, the pridopidine is administered daily. In one embodiment, the pridopidine is administered once daily. In another embodiment, the pridopidine is administered more often than once daily. In one embodiment, the pridopidine is administered twice daily.

In some embodiments, the pharmaceutical composition disclosed herein comprises pridopidine or a pharmaceutically acceptable salt thereof and at least one of Compounds 1-8 or pharmaceutically acceptable salt thereof for use in the methods of this invention is administered in a daily dose of between 0.5-315 mg pridopidine or a pharmaceutically acceptable salt thereof. In another embodiment, the composition is administered in a daily dose of 0.5-10 mg pridopidine or a pharmaceutically acceptable salt thereof. In another embodiment, the composition is administered in a daily dose of 10-22.5 mg pridopidine or a pharmaceutically acceptable salt thereof. In another embodiment, the composition is administered in a daily dose of 22.5-315 mg pridopidine or a pharmaceutically acceptable salt thereof. In another embodiment, the composition is administered in a daily dose 10-315 mg pridopidine or a pharmaceutically acceptable salt thereof. In another embodiment, the composition is administered in a daily dose 0.5-50 mg pridopidine or a pharmaceutically acceptable salt thereof. In another embodiment, the composition is administered in a daily dose 22.5-315 mg pridopidine or a pharmaceutically acceptable salt thereof. In another embodiment, the composition is administered in a daily dose 45-250 mg pridopidine or a pharmaceutically acceptable salt thereof. In another embodiment, the composition is administered in a daily dose 45-135 mg pridopidine or a pharmaceutically acceptable salt thereof. In another embodiment, the composition is administered in a daily dose 90-315 mg pridopidine or a pharmaceutically acceptable salt thereof.

In another embodiment, the amount of pridopidine administered is about 1 mg/day, about 5 mg/day, about 10 mg/day, 20 mg/day, 22.5 mg/day, about 45 mg/day, about 67.5 mg/day, about 90 mg/day, about 100 mg/day, about 112.5 mg/day, about 125 mg/day, about 135 mg/day, about 150 mg/day, about 180 mg/day, about 200 mg/day, about 225 mg/day, about 250 mg/day, or about 315 mg/day.

In an embodiment, the amount of pridopidine administered is 45 mg/day. In an embodiment, the amount of pridopidine administered is 90 mg/day. In an embodiment, the amount of pridopidine administered is 180 mg/day. In an embodiment, the amount of pridopidine administered is 225 mg/day.

In one embodiment, the pharmaceutical composition disclosed herein is administered once a day. In one embodiment, the pharmaceutical composition disclosed herein is administered twice a day.

In one embodiment, the pharmaceutical composition disclosed herein is administered in a dose of about 1 mg, about 5 mg, about 10 mg, about 22.5 mg, about 45 mg, about 67.5 mg, about 90 mg, about 100 mg, about 112.5 mg, about 125 mg, about 135 mg, about 150 mg, about 180 mg, about 200 mg, about 250 mg, or about 315 mg of pridopidine. In an embodiment, the amount of pridopidine administered within the composition is 45 mg. In an embodiment, the amount of pridopidine administered within the composition disclosed herein is 10-45 mg.

In one embodiment, the composition disclosed herein is administered twice a day, wherein each composition comprises an amount of 45 mg pridopidine per dose.

In one embodiment, the pharmaceutical composition disclosed herein is first administered from as from as early as 1 day after birth and older. In one embodiment, the pharmaceutical composition disclosed herein is first administered within 1 day after birth of the subject. In one embodiment, the pharmaceutical composition disclosed hereine is first administered within 1 week after birth of the subject. In one embodiment, the pharmaceutical composition disclosed herein is first administered within 1 month after birth of the subject. In one embodiment, the pharmaceutical composition disclosed herein is first administered within 3 months after birth of the subject. In one embodiment, the pharmaceutical composition disclosed herein is first administered within 6 months after birth of the subject. In one embodiment, the pharmaceutical composition disclosed herein is first administered within 9 months after birth of the subject. In one embodiment, the pharmaceutical composition disclosed herein is first administered within 12 months after birth of the subject. In one embodiment, the pharmaceutical composition disclosed herein is first administered within 18 months after birth of the subject. In one embodiment, the pharmaceutical composition disclosed herein is first administered within 3 years after birth of the subject. In one embodiment, the pharmaceutical composition disclosed herein is first administered within 5 years after birth of the subject. In one embodiment, the pharmaceutical composition disclosed herein is first administered within 10 years after birth of the subject. In one embodiment, the pharmaceutical composition disclosed herein is first administered within 15 years after birth of the subject. In one embodiment, the pharmaceutical composition disclosed herein is first administered within 20 years after birth of the subject. In one embodiment, the pharmaceutical composition disclosed herein is first administered within 25 years after birth of the subject. In one embodiment, the pharmaceutical composition disclosed herein is first administered within 30 years after birth of the subject. In one embodiment, the pharmaceutical composition disclosed herein is first administered 30 years or more after birth of the subject.

In one embodiment, the periodic administration of the pharmaceutical composition disclosed herein continues for at least 3 days, at least 30 days, at least 42 days, at least 8 weeks, at least 12 weeks, at least 24 weeks, at least 6 months, at least 1 year, at least 2 years, at least 5 years, at least 10 years, at least 15 years, at least 20 years, at least 25 years, or 30 years or more.

In one embodiment, the pharmaceutical composition disclosed herein treats the subject by delaying the onset of symptoms in the subject.

In one embodiment, the pharmaceutical composition disclosed herein is used for treating a subject afflicted with Rett syndrome by delaying the onset, preventing worsening, delaying worsening, or improving of at least one symptom in the subject. In one embodiment, pharmaceutical composition disclosed herein improves or delays the worsening of at least one symptom in the subject afflicted with Rett syndrome. In one embodiment, the pridopidine pharmaceutical composition disclosed herein treats the subject by improving at least one symptom in the subject.

In some embodiments, this invention is directed to a method of delaying the onset, preventing worsening, delaying worsening or improving at least one RTT symptom in the subject, by administering a pharmaceutical composition comprising pridopidine or a pharmaceutically acceptable salt thereof and at least one of compounds 1-8 or pharmaceutically acceptable salt thereof, wherein the RTT symptom is abnormal gait, ataxia, impaired gait initiation delay in acquiring purposeful hand skills or a partial or complete loss of acquired purposeful hand skills, or the symptom is abnormal hand movement, startle response or delayed crawling, and/or walking; decreased ability to crawl, and/or walk; or abnormal eye movement.

In one embodiment, the symptom is a delay in acquiring mobility skills. In one embodiment, the symptom is delayed sitting, crawling, and/or walking. In one embodiment, the symptom is a partial or complete loss of acquired mobility skills. In one embodiment, the symptom is decreased ability to sit, crawl, and/or walk. In one embodiment, the mobility skill is motor coordination skill.

In one embodiment, the symptom is abnormal gait. In one embodiment, the symptom is ataxia. In one embodiment, the symptom is apraxia. In one embodiment, the symptom is muscle weakness.

In one embodiment, the symptom is spasticity. In one embodiment, the symptom is rigidity. In one embodiment, the symptom is impaired gait initiation.

In one embodiment, the symptom is abnormal muscle tone. In one embodiment, the symptom is hypotonia. In one embodiment, the symptom is peripheral vasomotor disturbance. In one embodiment, the symptom is scoliosis. In one embodiment, the symptom is impaired gait initiation.

In one embodiment, the symptom is a delay in acquiring purposeful hand skills. In one embodiment, the symptom is a partial or complete loss of acquired purposeful hand skills. In one embodiment, the symptom is abnormal hand movement. In one embodiment, the abnormal hand movement is wringing, squeezing, clapping, washing, tapping, rubbing, and/or repeatedly bringing hands to mouth.

In one embodiment, the symptom is a delay in acquiring communication skills. In one embodiment, the symptom is a partial or complete loss of acquired communication skills. In one embodiment, the communication skill is language skill. In one embodiment, the language skill is spoken language skill. In one embodiment, the communication skill is eye contact.

In one embodiment, the symptom is abnormal eye movement. In one embodiment, the abnormal eye movement is prolonged staring, excessive blinking, crossed eyes, and/or closing one eye at a time.

In one embodiment, the symptom is breathing irregularity. In one embodiment, the breathing irregularity occurs when the subject is awake. In one embodiment, the breathing irregularity is apnea. In one embodiment, the breathing irregularity is hyperventilation.

In one embodiment, the symptom is bruxism when the subject is awake.

In one embodiment, the symptom is increased irritability, decreased alertness, and/or decreased attention span. In one embodiment, the symptom is inappropriate laughing and/or screaming.

In one embodiment, the symptom is seizure.

In one embodiment, the symptom is cardiac abnormality. In one embodiment, the cardiac abnormality is bradycardia. In one embodiment, the cardiac abnormality is tachycardia.

In one embodiment, the symptom is decreased response to pain. In one embodiment, the symptom is growth retardation. In one embodiment, the symptom is microcephaly. In one embodiment, the symptom is impaired sleeping pattern. In one embodiment, the symptom is hypotrophic cold blue feet.

In one embodiment, the pharmaceutical composition disclosed herein improves the symptom by at least 5%. The composition improves the symptom by at least 10%. In one embodiment, the composition improves the symptom by at least 20%. In one embodiment, the composition improves the symptom by at least 30%. In one embodiment, the composition improves the symptom by at least 50%. In one embodiment, the composition improves the symptom by at least 80%. In one embodiment, the composition improves the symptom by 100%.

In one embodiment, the pharmaceutical composition disclosed herein is used for treating the subject by improving the subject's ability to perform activities of daily living, perform domestic chores, manage finances, and/or perform an occupation. In one embodiment, the pharmaceutical composition disclosed herein is used for treating the subject by reducing the level of nursing care needed by the subject.

In one embodiment, the pharmaceutical composition disclosed herein is used for treating the subject by maintaining the subject's ability to perform activities of daily living, perform domestic chores, manage finances, and/or perform an occupation.

In one embodiment, the pharmaceutical composition disclosed herein is effective to increase the BDNF serum level in the subject. In one embodiment, the composition is effective to increase the BDNF levels in the brain of the subject. In one embodiment, the composition is effective to maintain the BDNF serum level in the subject.

This invention also provides a pharmaceutical composition comprising an amount of pridopidine for use in treating a subject afflicted with RTT.

This invention also provides a pharmaceutical composition in unit dosage form, useful in treating a subject afflicted with RTT.

In one embodiment, the amount of pridopidine administered 0.5 mg/day-315 mg/day. In one embodiment, the amount of pridopidine is 10 mg-315 mg. In one embodiment, the amount of pridopidine is 90 mg-315 mg. In one embodiment, the amount of pridopidine is 90 mg-225 mg. In another embodiment, the amount of pridopidine is about 22.5 mg, about 45 mg, about 67.5 mg, about 90 mg, about 100 mg, about 112.5 mg, about 125 mg, about 135 mg, about 150 mg, about 180 mg, about 200 mg, about 225 mg, about 250 mg, or about 315 mg. In an embodiment, the amount of pridopidine is 45 mg. In an embodiment, the amount of pridopidine is 90 mg. In an embodiment, the amount of pridopidine is 180 mg. In an embodiment, the amount of pridopidine is 225 mg.

This invention also provides a use of a pharmaceutical composition disclosed herein in the manufacture of a medicament for treating a subject afflicted with RTT.

This invention also provides a use of an amount of pridopidine for treating a subject afflicted with RTT.

This invention also provides a method of increasing BDNF levels in serum in a subject afflicted with RTT comprising administering to the subject a pharmaceutical composition disclosed herein so as to thereby increase BDNF serum level in the subject. This invention also provides a method of increasing BDNF brain level in a subject afflicted with RTT comprising administering to the subject an pharmaceutical composition disclosed herein so as to thereby increase BDNF levels in the brain of the subject.

For the foregoing embodiments, each embodiment disclosed herein is contemplated as being applicable to each of the other disclosed embodiments. In addition, the elements recited in method embodiments can be used in the pharmaceutical composition, use, and package embodiments described herein and vice versa.

Pharmaceutical Composition for Use in the Methods of this Invention:

In some embodiments the methods of this invention make use of a pharmaceutical composition comprising pridopidine or pharmaceutically acceptable salt thereof and at least one of compounds 1-8

(Compound 1)

$SO_2CH_3$, OH, N ,

-continued (Compound 2)

$SO_2CH_3$, $SO_2CH_3$, N, $SO_2CH_3$, (Compound 3)

$O_2S$, $SO_2$, N, Pr, N, Pr, (Compound 4)

$SO_2CH_3$, OH, N , (Compound 5)

$SO_2CH_3$, $O^-$, $N^+$ , (Compound 6)

$SO_2CH_3$, N , (Compound 7)

$SOCH_3$, N , or

-continued (Compound 8)

$SO_2CH_3$ or pharmaceutically acceptable salt thereof.

In other embodiments the methods of this invention make use of a pharmaceutical composition comprising pridopidine or pharmaceutically acceptable salt thereof and compound 1 or pharmaceutically acceptable salt thereof.

In other embodiments the methods of this invention make use of a pharmaceutical composition comprising pridopidine or pharmaceutically acceptable salt thereof and compound 2 or pharmaceutically acceptable salt thereof.

In other embodiments the methods of this invention make use of a pharmaceutical composition comprising pridopidine or pharmaceutically acceptable salt thereof and compound 3 or pharmaceutically acceptable salt thereof.

In other embodiments the methods of this invention make use of a pharmaceutical composition comprising pridopidine or pharmaceutically acceptable salt thereof and compound 4 or pharmaceutically acceptable salt thereof.

In other embodiments the methods of this invention make use of a pharmaceutical composition comprising pridopidine or pharmaceutically acceptable salt thereof and compound 5 or pharmaceutically acceptable salt thereof.

In other embodiments the methods of this invention make use of a pharmaceutical composition comprising pridopidine or pharmaceutically acceptable salt thereof and compound 6 or pharmaceutically acceptable salt thereof.

In other embodiments the methods of this invention make use of a pharmaceutical composition comprising pridopidine or pharmaceutically acceptable salt thereof and compound 7 or pharmaceutically acceptable salt thereof.

In other embodiments the methods of this invention make use of a pharmaceutical composition comprising pridopidine or pharmaceutically acceptable salt thereof and compound 8 or pharmaceutically acceptable salt thereof.

In other embodiments the methods of this invention make use of a pharmaceutical composition comprising pridopidine or a pharmaceutically acceptable salt thereof and at least one of compound 1, compound 4, pharmaceutically acceptable salt thereof or combination thereof.

In other embodiments the methods of this invention make use of a pharmaceutical composition comprising pridopidine or a pharmaceutically acceptable salt thereof and compound 1 or pharmaceutically acceptable salt thereof.

In other embodiments the methods of this invention make use of a pharmaceutical composition comprising pridopidine or a pharmaceutically acceptable salt thereof and compound 4 or pharmaceutically acceptable salt thereof.

In other embodiments the methods of this invention make use of a pharmaceutical composition comprising pridopidine or a pharmaceutically acceptable salt thereof, compound 1 and compound 4 or pharmaceutically acceptable salt thereof.

In other embodiments the methods of this invention make use of a pharmaceutical composition comprising pridopidine salt, wherein the salt is hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

In other embodiments the methods of this invention make use of a pharmaceutical composition comprising at least one of compounds 1-8 salt, wherein the salt is hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

In other embodiments the methods of this invention make use of a pharmaceutical composition, wherein the composition is an oral dosage unit comprising between 0.5-315 mg pridopidine or pharmaceutically acceptable salt thereof. In other embodiments, the oral dosage unit form comprises between 0.5-10 mg pridopidine. In other embodiments, the oral dosage unit form comprises between 10-22.5 mg pridopidine. In other embodiments, the oral dosage unit form comprises between 22.5-45 mg pridopidine. In other embodiments, the oral dosage unit form comprises between 45-250 mg pridopidine. In other embodiments, the oral dosage unit form comprises between 45-135 mg pridopidine. In other embodiments, the oral dosage unit form comprises between 90-315 mg pridopidine.

In other embodiments the methods of this invention make use of a pharmaceutical composition comprising pridopidine or pharmaceutically acceptable salt thereof and at least one of compounds 1-8 or pharmaceutically acceptable salt thereof, wherein the weight ratio between the pridopidine and at least one of compounds 1-8 is in the range of 1:0.0001 to 1:0.1. In other embodiments, the weight ratio between the pridopidine and at least one of compounds 1-8 is in the range of 1:0.005 to 1:0.1. In other embodiment, the weight ratio between the pridopidine and at least one of compounds 1-8 is in the range of 1:0.001 to 1:0.005. In other embodiments, the concentration of compounds 1, 2, 3, 4, 5, 6, 7 or 8 or pharmaceutically acceptable salt thereof within the composition is between 0.01% w/w to 10% w/w. In other embodiments, the concentration of compounds 1, 2, 3, 4, 5, 6, 7 or 8 or pharmaceutically acceptable salt thereof within the composition is between 0.01% w/w to 0.05% w/w. In other embodiments, the concentration of compounds 1, 2, 3, 4, 5, 6, 7 or 8 or pharmaceutically acceptable salt thereof within the composition is between 0.01% w/w to 0.5% w/w. In other embodiments, the concentration of compounds 1, 2, 3, 4, 5, 6, or 8 or pharmaceutically acceptable salt thereof within the composition is between 0.01% w/w to 0.15% w/w. In other embodiments, the concentration of compounds 1, 2, 3, 4, 5, 6, 7 or 8 or pharmaceutically acceptable salt thereof within the composition is between 0.01% w/w to 0.15% w/w. In other embodiments, the concentration of compounds 1, 2, 3, 4, 5, 6, or 8 or pharmaceutically acceptable salt thereof within the composition is between 0.01% w/w to 0.5% w/w. In other embodiments, the concentration of compounds 1, 2, 3, 4, 5, 6, 7 or 8 or pharmaceutically acceptable salt thereof within the composition is between 0.01% w/w to 1% w/w. In other embodiments, the concentration of compounds 1, 2, 3, 4, 5, 6, 7 or 8 or pharmaceutically acceptable salt thereof within the composition is between 0.05% w/w to 0.2% w/w. In other embodiments, the concentration of compounds 1, 2, 3, 4, 5, 6, 7 or 8 or pharmaceutically acceptable salt thereof within the composition is between 0.05% w/w to 0.3% w/w. In other embodiments, the concentration of compounds 1, 2, 3, 4, 5, 6, 7 or 8 or pharmaceutically acceptable salt thereof within the composition is between 0.05% w/w to 0.4% w/w.

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries. In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in multiparticulates, in powder, or in liquid form, and parenteral administration, in particular cutaneous, subcutaneous, intramuscular, or intravenous injection. The pharmaceutical composition for use in the methods of this invention is an oral dosage unit formulated as a tablet, a capsule, a pill, powder, multiparticulates in capsule or sachet, liquid solution or as a liquid suspension.

Terms

As used herein, and unless stated otherwise, each of the following terms shall have the definition set forth below.

As used herein, "pridopidine" means pridopidine base or a pharmaceutically acceptable salt thereof, as well as derivatives or analogs thereof, for example deuterium-enriched pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference.

"Deuterium-enriched" means that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%. Deuterium-enriched compounds may be obtained by exchanging hydrogen with deuterium or synthesizing the compound with deuterium-enriched starting materials.

The active compound for use according to the invention may be provided in any form suitable for the intended administration. Suitable forms include pharmaceutically acceptable salts, and pre- or prodrug forms of the compound of the invention.

A "salt thereof" is a salt of the instant compound which has been modified by making acid or base salts of the compound. The term "pharmaceutically acceptable salt" in this respect, refers to the relatively non-toxic, inorganic and organic acid or base addition salts of compound of the present invention suitable for pharmaceutical use. Pharmaceutically acceptable salts may be formed by procedures well known and described in the art. One means of preparing such a salt is by treating a compound of the present invention with an inorganic base.

Examples of acid addition salts of the compound of the present invention include, but is not limited to, the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. In certain embodiments, pridopidine is a pharmaceutically acceptable salt, such as the HCl salt or tartrate salt. Preferably, in any embodiments of the invention as described herein, the pridopidine is in the form of its hydrochloride salt.

As used herein, an "amount" or "dose" of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine in a preparation is 90 mg, regardless of the form of the preparation. Thus, when in the form of a salt, e.g. pridopidine hydrochloride, the weight of the salt form necessary to provide a dose of 90 mg pridopidine would be greater than 90 mg due to the presence of the salt.

As used herein, a "unit dose", "unit doses" and "unit dosage form(s)" mean a single drug administration entity/entities. A "unit dose", "unit doses" and "unit dosage form (s)" can be prepared for oral dosage forms, such as tablets, capsules, pills, powders, and granules.

As used herein, "about" in the context of a numerical value or range means 90-110% of the numerical value or range recited or claimed.

"Administering to the subject" or "administering to the (human) patient" means the giving of, dispensing of, or application of medicines, drugs, or remedies to a subject/patient to delay, relieve, cure, or reduce the symptoms associated with a condition, e.g., a pathological condition. Oral administration is one way of administering the instant compounds to the subject.

A compound according to the subject invention may be administered in the base form or in the form of pharmaceutically acceptable salts, preferably in a pharmaceutical composition together with one or more adjuvants, excipients, carriers, buffers, diluents, and/or other customary pharmaceutical auxiliaries.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compound to the subject.

The administration can be periodic administration. As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times weekly and so on, etc.

"Treat" or "treating" as used herein encompasses alleviating, lessening, reducing the severity of, eliminating or substantially eliminating, or ameliorating a physical, mental or emotional limitation in a subject afflicted with RTT.

Treating also refers to delaying or prevention of symptoms or reduction of deficits associated with a disease.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a symptom of Rett Syndrome. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

It is understood that where a parameter range is provided, all integers within that range, and tenths thereof, are also provided by the invention. For example, "22 mg-300.0 mg" includes 22.0 mg, 22.1 mg, 22.2 mg, 22.3 mg, 22.4 mg, etc. up to 300.0 mg inclusive.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: Evaluation of the Efficacy of Pridopidine in the Heterozygous MeCP2 Female Mouse Model of Rett Syndrome The goal of this study was to assess the effects of pridopidine in the female MeCP2-Het (BIRD) mouse model of Rett Syndrome (Guy 2001).

Materials:

Pridopidine (3 and 30 mg/kg) was administered orally twice daily (6 hours between dosing) at a dose volume of 10 ml/kg. On test days, pridopidine was administered 30 minutes prior to test.

Dosing commenced when mice were ~5.5 weeks of age and continued through the end of behavioral testing. Behavioral testing was done at 8 and 12 weeks of age.

Female MeCP2 (MeCP2_HET, Rett) mice and wild type (MeCP2_WT, WT) littermates were housed at 20-23° C. with 50% relative humidity, and a 12/12 light/dark cycle. Chow and water were provided ad libitum. All tests were performed during the light phase. Animals were examined and weighed throughout the study to assure adequate health and suitability and to minimize nonspecific stress associated with manipulation. All animals were examined and weighed prior to initiation and throughout the study to assure adequate health and suitability and to minimize nonspecific stress associated with manipulation. During the course of the study, 12/12 light/dark cycle was maintained. The room temperature was maintained between 20 and 23° C. with a relative humidity maintained around 50%. Chow and water were provided ad libitum for the duration of the study. The tests were performed during the animal's light cycle phase.

Methods:

Treatment Groups:

- WT mice—vehicle (saline), n=24
- Rett HET MeCP2 mice—vehicle (, saline), n=24
- Rett HET MeCP2 mice—Pridopidine (3 mg/kg; orally twice daily, bid), n=20
- Rett HET MeCP2 mice—Pridopidine (30 mg/kg; orally twice daily, bid), n=20

Behavioral Tests:

(1) Gait Analysis Using NeuroCube® System

The NeuroCube® system is a platform that employs computer vision to detect changes in gait geometry and gait dynamics in rodent models of neurological disorders, pain & neuropathies. This platform is unique for gait testing for the following reasons:

- It is completely automated and thus removes any bias or subjectivity
- This system captures both gait geometry and gait dynamics (stance, swing, propulsion, etc.)

Mice were placed in the NeuroCube for a 5 min test. The most dominant of the features collected that define the disease phenotype (symptom descriptors) was identified and ranked. Complex bioinformatic algorithms were employed to calculate the discrimination probability between the WT and the Rett HET MeCP2 mice and detect a test compound's ability to reverse the disease phenotype. Discriminations between mutant and wild type was calculated as well as the recovery of disease features in Rett HET MeCP2 mice treated with the test compound.

(2) Clasping

Clasping is used to assess muscular strength in limb muscles. Mice were held by the tail and gently lifted until the front paws just lift off the counter surface. The experimenter observed the legs and determined clasping or splaying of limbs. After testing, animals were placed back into the test or home cage. Percent clasping of the hindlimbs was determined and reported.

(3) Startle Response/Prepulse Inhibition (PPI)

The acoustic startle measures an unconditioned reflex response to external auditory stimulation. Prepulse inhibition (PPI) consisting of an inhibited startle response (reduction in amplitude) to an auditory stimulation following the presentation of a weak auditory stimulus or prepulse, has been used as a tool for the assessment of deficiencies in sensory-motor gating, such as those seen in schizophrenia.

Mice were placed in the PPI chambers (Med Associates) for a 5 min session of white noise (70 dB) habituation. After the acclimation period the test session automatically started. The session started with a habituation block of 6 presentations of the startle stimulus alone, followed by 10 PPI blocks of 6 different types of trials.

Trial types were: null (no stimuli), startle (120 dB), startle plus prepulse (4, 8 and 12 dB over background noise i.e. 74, 78 or 82 dB) and prepulse alone (82 dB). Trial types were presented at random within each block. Each trial started with a 50 ms null period during which baseline movements were recorded. There was a subsequent 20 ms period during which prepulse stimuli were presented and responses to the prepulse were measured. After further 100 ms the startle stimuli were presented for 40 ms and responses recorded for 100 ms from startle onset. Responses were sampled every millisecond. The inter-trial interval was variable with an average of 15 s (range from 10 to 20 s).

In startle alone trials the basic auditory startle was measured and in prepulse plus startle trials the amount of inhibition of the normal startle was determined and expressed as a percentage of the basic startle response (from startle alone trials), excluding the startle response of the first habituation block.

Brain Collection:

After all behavioral testing was completed brain samples were collected 60 minutes after dosing with pridopidine. Mice were euthanized via cervical dislocation and decapitated. From 10 mice/treatment group, whole brains were collected, weighed, and then frozen on dry ice. Samples were stored at −80° C. until analysis of brain-derived neurotrophic factor (BDNF).

BDNF Analysis:

Total RNA Extraction:

Tissues (whole brain) were homogenized, and RNA extracted and quantified. An aliquote was reverse-transcribed into cDNA.

Up to three independent RT reactions were performed for each RNA sample. qPCR was performed using the primers detailed in Table 5 below.

TABLE 5 qPCR and primers/probe information

| Mouse Gene ID | 5′ Primer Sequence | 3′ Primer Sequence | Universal Probe Library # | Tissue | PCR Efficiency |
|---|---|---|---|---|---|
| ATP5B | GGCACAATGCAGGAAAGG (SEQ ID NO: 1) | TCAGCAGGCACATAGATAGCC (SEQ ID NO: 2) | 77 | Brain | 1.89 |
| RPL13A | TTGTGGCCAAGCAGGTACT (SEQ ID NO: 3) | GTTGATGCCTTCACAGCGTA (SEQ ID NO: 4) | 77 | Brain | 1.91 |
| GAPDH | CAATGTGTCCGTCGTGGATCT (SEQ ID NO: 5) | GTCCTCAGTGTAGCCCAAGATG (SEQ ID NO: 6) | N/A | Brain | 1.87 |
| BDNF I | AGTCTCCAGGACAGCAAAGC (SEQ ID NO: 7) | TGCAACCGAAGTATGAAATAACC (SEQ ID NO:8) | 31 | Brain | 2.00 |
| BDNF IV | GCTGCCTTGATGTTTACTTTGA (SEQ ID NO: 9) | AAGGATGGTCATCACTCTTCTCA (SEQ ID NO:10) | 31 | Brain | 2.04 |
| BDNF VI | CCGAGAGCTTTGTGTGGAC (SEQ ID NO: 11) | TCATGCAACCGAAGTATGAAA (SEQ ID NO: 12) | 31 | Brain | 1.93 |
| BDNF IX | GCCTTTGGAGCCTCCTCTAC (SEQ ID NO: 13) | GCGGCATCCAGGTAATTTT (SEQ ID NO: 14) | 67 | Brain | 2.01 |

qPCR Data Analysis:

Whole brain cDNA prepared from a pooled sample of WT vehicle treated animals was used as calibrator (calibrator is diluted same as sample cDNA) to normalized plate-to-plate variations. Each cDNA sample (diluted 1:10) was assayed in triplicates and the Ct values averaged. Values that lie greater than 0.5 standard deviation of the average were discarded.

Relative quantity of the PCR product (relative to the calibrator) was calculated as follows:

$$\text{Relative Quantity of Target gene}=(PCR\ \text{EfficiencyTarget})^{(Ct\ calibrator-Ctsample)}$$

$$\text{Relative Quantity of Housekeeping Gene1}=(PCR\ \text{Efficiencyhousekeeping1})^{(Ct\ calibrator-Ctsample)}$$

$$\text{Relative Quantity of Housekeeping Gene2}=(PCR\ \text{Efficiencyhousekeeping2})^{(Ct\ calibrator-Ctsample)}$$

$$\text{Relative Quantity of Housekeeping Gene3}=(PCR\ \text{Efficiencyhousekeeping3})^{(Ct\ calibrator-Ctsample)}$$

Geometric mean for the three housekeeping genes was calculated as follows:

$$\text{Geometric mean}=(\text{relative quantity of housekeeping gene1}*\text{relative quantity of housekeeping gene2}*\text{relative quantity of housekeeping gene3})^{(1/3)}$$

Relative level of target gene was calculated as follows:

Relative Quantity of Target gene Geometric mean of housekeeping genes

Relative level of target gene was then normalized to the WT vehicle group.

Statistical Analysis:

Data from standard tests were analyzed by genotype (t-test) and by treatment (ANOVA) followed by post-hoc comparisons where appropriate. For some measures, repeated-measures ANOVAs were performed. For clasping data, N-1 two-proportional tests were performed. An effect was considered significant if $p<0.05$. All data are represented as the mean and standard error to the mean (s.e.m). Values±2 standard deviations from the mean were considered outliers.

Data analysis from NeuroCube:

The output of NeuroCube is a set of dozens of behavioral features that are submitted for analysis with machine learning techniques used in bioinformatics. Many of these features are correlated (e.g. rearing counts and supported rearing counts). Therefore, PGI forms statistically independent combinations of the original features (further referred to as de-correlated features) that discriminate between the two groups more effectively.

Each de-correlated feature extracts information from the whole cluster of the original features, so the new feature space has lower dimensionality. Next, PGI applies a proprietary feature ranking algorithm to score each feature's discrimination power (ability to separate the two groups, e.g. control and disease).

Ranking is an important part of the analyses because it weighs each feature change by its relevance: if there is a significant change in some irrelevant feature measured for a particular phenotype, the low rank of this feature will automatically reduce the effect of such change in the analyses, so there is no need to resort to the conventional "feature selection" approach and discard information buried in the less informative features. Ranking algorithm can be applied to either original or the new features to gain insight about the key control-disease differences.

Feature Analysis: Quantitative Assessment of Disease Phenotype

In the new feature space, the overlap between the "clouds" (Gaussian distributions approximating the groups of mice in the ranked de-correlated features space) serves as a quantitative measure of separability ("distinguishability") between the two groups. For visualization purposes, each cloud was plotted with its semi-axes equal to the one standard deviation along the corresponding dimensions.

Results:

Behavioral Tests:

(1) Clasping

Rett Syndrome patients lose or fail to acquire purposeful hand movements, and these are replaced by stereotypical movements such as hand wringing. In the Rett mouse model, this symptom correlates with a hindlimb clasping phenotype. Rett model mice show significantly more clasping compared to the WT mice (FIG. 2). Pridopidine improves clasping at 8 weeks as shown in FIG. 2. Vehicle-treated RETT mice show significantly more clasping compared to the WT mice. Pridopidine (30 mg/kg bid) normalizes this behavior ($p<0.06$) at 8 weeks. At 8 weeks, columns representing the WT vehicle treated and pridopidine treated (30 mg/kg bid) animals are zero. This suggests that pridopidine 30 mg/kg bid is efficacious for treating this symptom, and may delay its onset.

(2) Startle Response/PPI

Rett Syndrome symptoms reduced alertness and attention span are recapitulated in the mouse model and assessed using the acoustic startle response. Vehicle-treated Rett mice show a significant inhibition in startle response compared to WT mice, by ~65% and ~75% at 8 and 12 weeks, respectively ($p<0.05$). Pridopidine (3 mg/kg bid) has a significant beneficial effect on the startle response of ~40% and ~50% at 8 and 12 weeks, respectively ($p<0.05$) as shown in FIG. 3.

(3) NeuroCube®

The discrimination probability between WT and Rett mice at 8 and 12 weeks of age was 90% and 94%, respectively. Some of the top gait features that discriminated between WT and Rett include longer stride and step length, narrower base width, and less paw intensity of WT mice compared to Rett mice.

Figure 4:
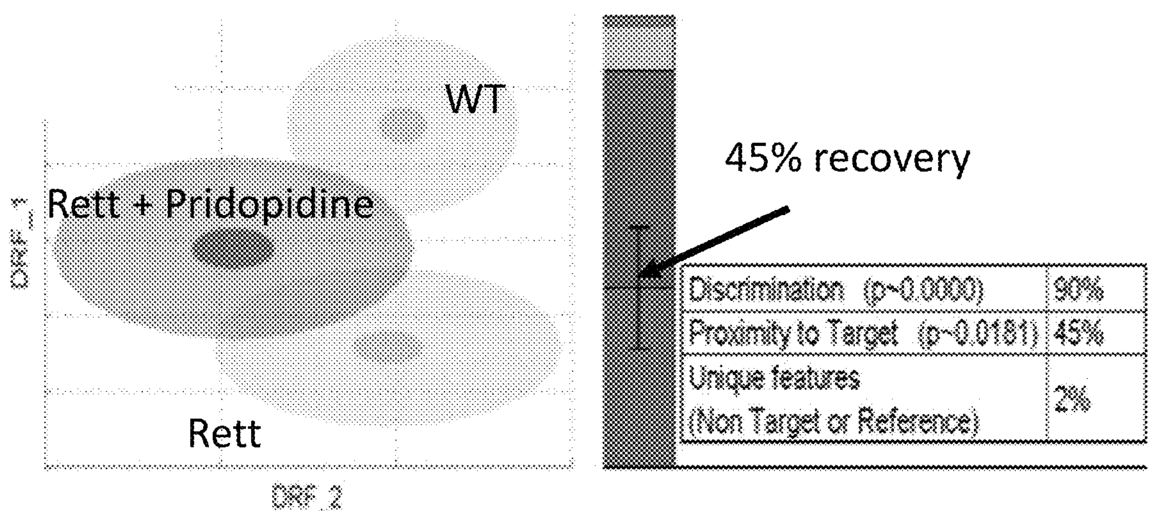

The effects of pridopidine on gait performance at 8 weeks are shown in FIG. 4. The effects of pridopidine on gait performance at 12 weeks are shown in FIG. 5. Pridopidine (30 mg/kg bid) shows significant recovery of overall gait features at both 8 weeks and 12 weeks (45% and 55%, respectively).

Further analysis shows significant differences in specific gait domains as shown in Table 5 below. The Rett mice were significantly different from the WT control mice overall, in all gait features. Week 8 data show that pridopidine (3 and 30 mg/kg bid) improves body motion and gait alone in Rett mice. Pridopidine treatment (3 mg/kg bid) significantly improves gait alone and body motion at 12 weeks. Significant effects on gait alone, body motion and paw positioning are also seen with pridopidine (30 mg/kg bid) at 12 weeks.

TABLE 6

Effects of pridopidine on gait at 8 and 12 weeks.

| | Feature | % Discrimination WT vs MeCP2-Het | % Recovery 3 mg/kg BID | % Recovery 30 mg/kg BID |
|---|---|---|---|---|
| 8 weeks | Gait | 92%, p = 0 | 38%, p = 0.022 | 71%, p = 0.004 |
| | Body Motion | 79%, p = 0.001 | 81%, p = 0.003 | 84%, p = 0.01 |
| 12 weeks | Gait | 94%, p = 0 | 60%, p = 0.005 | 100%, p = 0 |
| | Body Motion | 83%, p = 0 | 65%, p = 0.021 | 59%, p = 0.041 |
| | Paw Positioning | 87%, p = 0.001 | 35%, p = 0.192 | 52%, p = 0.032 |

BDNF Analysis

The effects of pridopidine on relative BDNF expression in brain samples of the WT and Rett mice are shown in FIGS. 6-10.

Whole brain control housekeeping genes mRNA expression levels do not change between the different animal groups treatments examined (see FIGS. 6A-6C).

As compared with WT (vehicle), BDNF I mRNA expression is significantly decreased by ~20% in Rett (vehicle) treated group ($p<0.001$). Pridopidine treatment (3 or 30 mg/kg bid) does not affect levels of BDNF I mRNA in Rett mice (see FIG. 7).

As compared with WT (vehicle), BDNF IV mRNA expression is significantly decreased in Rett (vehicle) treated group by ~15% ($p<0.01$). Pridopidine treatment (3 or 30 mg/kg bid) rescues downregulated BDNF IV mRNA in Rett mice by ~30%, close to WT levels ($p<0.001$) (see FIG. 8 8).

As compared with WT (vehicle), BDNF VI mRNA expression was significantly decreased in Rett (vehicle) treated group by ~25% ($p<0.05$). Pridopidine treatment (3 or 30 mg/kg bid) does not affect levels of BDNF VI mRNA in Rett mice (see FIG. 9).

As compared with WT (vehicle), BDNF IX mRNA expression is significantly decreased by ~20% in Rett (vehicle) treated group ($p<0.0001$). Pridopidine treatment (3 or 30 mg/kg bid) rescues downregulated BDNF IX mRNA in Rett mice close to WT levels ($p<0.001$) (see FIG. 10).

Conclusion

This study evaluated the effects of chronic administration of pridopidine on gait, hindlimb clasping, and startle/PPI in Rett model mice.

Rett mice have distinct alterations in gait measures that discriminate them from WT mice. They also demonstrate stereotypic hindlimb clasping phenotype. Additionally, Rett mice demonstrate an inhibition in the acoustic startle response compared to WT mice. Pridopidine treatment significantly rescues hindlimb clasping at 8 weeks of age (30 mg/kg bid) and significantly improves the startle response compared to vehicle-treated Rett mice at 8 and 12 weeks (3 mg/kg bid). Rett mice treated with pridopidine (30 mg/kg bid) show significant recovery of gait features at 8 and 12 weeks.

Treatment with both doses of Pridopidine (3 and 30 mg/kg bid) fully rescues the downregulated mRNA levels of BDNF IV and BDNF IX. A Positive effect of Pridopidine on expression of BDNF mRNA is consistent with improvement observed in behavioral paradigms.

Example 2: RNA Analysis of Pridopidine Treated MeCP2 Mice

Methods:

Female Rett model mice (MeCP2 Heterozygotes) and wild type (WT) littermates at ~5.5 weeks of age were treated with either pridopidine or vehicle orally (per os, PO). Pridopidine (3 and 30 mg/kg bid) was administered orally twice daily (bid, 6 hours between dosing) at a dose volume of 10 ml/kg. There were four treatment groups: 1. WT mice—vehicle, 2. Rett mice—vehicle, 3. Rett mice—Pridopidine (3 mg/kg; bid), 4. Rett mice—Pridopidine (30 mg/kg; bid).

This experiment assessed whether pridopidine reverses aberrant transcription observed in the Rett mice. This was done by testing whether pridopidine restores the expression of genes perturbed in disease context back to WT levels. Additionally, the impact of pridopidine on gene expression in the Rett Syndrome mouse model was assessed.

Results:

Pridopidine Reverses Rett Syndrome Disease Gene Expression Signature in the Striatum and Cortex Analyzed by the Gene Set Enrichment Analysis (GSEA) Method

TABLE 7

Pridopidine reversal of gene expression signal in the striatum of Rett model mice

| Dose | Direction | Adj p value | Statistical test |
|---|---|---|---|
| 3 mg/kg BID | Down in Rett | 2.40E−04 | GSEA |
| 30 mg/kg BID | Up with Prido | 1.87E−03 | GSEA |

TABLE 8

Pridopidine reversal of gene expression signal in cortex of Rett model mice

| Dose | Direction | Adj p value | Statistical test |
|---|---|---|---|
| 3 mg/kg BID | Down in Rett | 2.71E−02 | GSEA |
| 30 mg/kg BID | Up with Prido | 6.20E−04 | GSEA |
| 3 mg/kg BID | Up in Rett | 7.66E−03 | GSEA |
| 30 mg/kg BID | Down with Prido | 4.26E−04 | GSEA |

Comparison of broad gene expression patterns reveals that pridopidine strongly reverses the gene expression pattern in both the striatum and cortex of Rett mice.

TABLE 9

Pridopidine reversal of Rett disease genes in the striatum

<table>
<tr><th>Geneset</th><th>Dose</th><th>NES</th><th>p.value</th><th>p.adjust</th><th>LeadingEdge</th></tr>
<tr><td>Up with Prido Down in Rett</td><td>3 mg/kg BID</td><td>−2.50</td><td>1.90E−04</td><td>2.40E−04</td><td>MAP3K6|ESR2|XIRP2|BHLHE22|SGK1|NEUROD1|BGLAP|SLC9A3|APOL6|FAM19A1|NPSR1|SIDT1|PLEKHF1|OTOG|VIP|CLON22|RTN4R|MEDAG|ARSI|MUC2|PTPN3|IRX2]ADAM33|GATA3|PRDM8|WISP2|C12orf50|SLC9A4|SIX4|TMEM215|PMCH|CD200R1L|HKDC1|CBLN4|MPL|SAMD7|WNT9A|LRRC17|HCRT|ADRA1D|SLC17A6|OXT|ZP2|CDHR2|ALOX12B|CHRNB3|PLCXD2|GRM2|ADRA18|TMEM145|TSPAN11|NPR3|KCNK4|TEX40|SCXB|NHLH2|AMDHD1|PTGDR|WNT6|C1R|ADCYAP1|ZNF648|SEC14L4|KCNAB3|ALDH3A1|CHRNA6|SYTL1|POZK1IP1|ETNK2|PLGJHES3|NEB</td></tr>
<tr><td>Down with Prido Up in Rett</td><td>3 mg/kg BID</td><td>2.18</td><td>2.11E−04</td><td>2.40E−04</td><td>DKK2|L3M&TL4|PHEX|KLHL10|CLSPN|CHST4|GALR1|LACTBL1|F9|CLDN23|CCR2|SLC10A4|RXRG|ARID3C|SLC26A5|CD300LG|SLFN12L|FGF3|CHAT|GPX6|CXCL10|ANXA10|PTPN7|LHX8|FXYD3|NEUROG1|TMPRSS11A|MYCT1|ZBP1|F2AL1|DCST1|NKX2-1|NR1I3|CNR2|GPR139|MYBPH|CHRNB4|PRSS56|SYT15|RYR1|STYK1|EDN1|ALAS2|OSM|PROKR1|SEC14L3|ZNF616|NXF3|TACR1</td></tr>
<tr><td>Up with Prido Down in Rett</td><td>30 mg/kg BID</td><td>−1.77</td><td>1.93E−04</td><td>1.87E−03</td><td>5PEM1|ESR2|ARC|SGK1|SPS] KLHL35|GRAP2|FPR2|TMPRSS6|C11orf96|8TG2|SNX31|MC3R|GUIS1|LTB|FMO2|GC|TFAP2B|DEFB130|TECTA|CKM|SLC25A25|FGA|FOSL2|CEBPD|CH25H|C6orf229|C6orf163|AOAH|CHIA|MIDN|CALCB|ZP2|SSUH2|GBX1|SAP25|TRIM29|NEUROD4|MGST2|ITK|HAAO|GUCY2C|CNGA3|MAFA|FAM83G|APOLD1|C17orf50|PAX5|C2orf74|SYTL1|PDZKIIP1|PLG|PCSK9|CRLF1</td></tr>
</table>

NES-normalized enrichment score

Table 9 shows that pridopidine 3 mg/kg bid reverses the Rett gene expression pattern in the striatum in both directions (upregulates genes that are down in Rett mice vs WT and down regulates genes that are up in Rett mice vs WT). Pridopidine 30 mg/kg bid significantly upregulated genes that are down in Rett mice vs WT.

TABLE 10

Pridopidine reversal of Rett disease genes in the Cortex

<table>
<tr><th>Geneset</th><th>Dose</th><th>NES</th><th>p.value</th><th>p.adjust</th><th>LeadingEdge</th></tr>
<tr><td>Prido Up Rett Down</td><td>3 mg/kg BID</td><td>1.477</td><td>2.30E−03</td><td>7.66E−03</td><td>NLRP10|CRABP1|ZAR1|CD300E|STK32B|MS4A15|CASR|MPZ|OPRM1|ATN1|GC|C11orf85|STOML3|STK31|C10orf53|GHSR|RHCG|MC4R|CYP19A1|C9orf171|CYP4A22|COL6A5|INSL6|PPM1J|S100A8|HLAA|SLC22A2|GPAT2|HP|CCDC170|PADI1|NMRK2|BRS3|SP110|TMEM252|TFAP2C|LSMEM2|TFPI2|OXGR1|SLC6A3|CCDC67|FSCN2|SLC38A8|CHRNB4|TMEM174|TMPRSS11A|SCN11A|GDPD4|CCDC38|SLC24A1|GNB3|MXD3|SPEM1|AIRE|ATF3|TAF7L</td></tr>
</table>

TABLE 10-continued

Pridopidine reversal of Rett disease genes in the Cortex

| Geneset | Dose | NES | p.value | p.adjust | LeadingEdge |
|---|---|---|---|---|---|
| Prido Down Rett Up | 3 mg · kg BID | 1.356 | 1.09E−02 | 2.71E−02 | CBLN2\|AKAP2\|PTPRQ\|ALAS2\|MEDAG\|ATOH7\|GGT6\|ARMC4\|TSHZ3\|PATL2\|TMEM88\|TRABD2B\|GALNT9\|DNAJC21\|SLCO1B3\|ANXA11\|CXCL6\|MKX\|XIRP2\|TMEM30B\|RXFP1\|SGK494\|AKR1C3\|C4orf22\|C3orf80\|TMEM178A\|LDB2\|CD7\|ADCY10\|EMILIN3\|CHRNA5\|ADRA1D\|GLT8D2\|OSBPL1A\|F2RL2\|PAMR1\|AMDHD1\|ZBP1\|CUZD1\|DKK3\|MYBPC1\|SYCE1L\|C14orf39\|GFRA2\|FEZF2\|HIST2H2BF\|CCBE1\|GCNT4\|VGLL3\|MBOAT4\|CA10\|KIAA0226L\|SERINC2\|MYLK3\|PKD1L2\|FHOD3\|HS3ST2\|ABRA\|EXPH5\|CHRNA1\|FAM132B\|TMEM232\|SATB2\|BMP8A\|BMP3\|B3GNT8\|SERPINB8\|COL12A1\|SLC9B2\|KRT80\|NEUROD6\|ADRA1B\|CCDC129\|PPARG\|FIGF\|ZNF296\|TRPV6\|LAYN\|ZBTB18\|TSKS\|NPC1L1\|FAP\|NTN5\|MICAL2\|CLDN23\|TBX22\|KRT7\|DNAH14\|PSRC1\|ARHGAP25\|PRDM8\|OVOL2\|PABPC4L\|C8orf46\|HERC6\|C1QL3\|HOPX\|MAGIX\|DDIT4L\|SLC26A4\|IRGC\|TSPAN11\|ADAM18\|GKN1\|CHRNB3\|NKX3-1\|ADRB3\|VIP\|IL12A\|KIAA1522\|C2CD4B\|RTN4R\|SYTL2 |
| Prido Up Rett Down | 30 mg/kg BID | −2.631 | 1.48E−04 | 4.26E−04 | EGR2\|BSPRY\|BAMBI\|LEFTY2\|CABYR\|KCNE4\|NGB\|PAPOLB\|RASL11A\|FUT2\|SPINK8\|ZNF189\|ARL4D\|DCN\|LYVE1\|SH2D6\|C1orf198\|RXFP3\|GFAP\|FOXR2\|CBX2\|ZAR1\|FOSL2\|MYO1A\|USP51\|STK32B\|WNT2B\|CASR\|ICOSLG\|CYBRD1\|KLC3\|FMO1\|GDPD2\|ATN1\|CCL24\|EFCAB1\|C15orf48\|CYR61\|ELF4\|NOV\|GHSR\|CEBPD\|MC4R\|MYOF\|LGALS12\|CKS1B\|ITGBL1\|ATOH8\|ADAD2\|MSH4\|CYP19A1\|CH25H\|SLC2A4\|TLR4\|SCNN1A\|ATP2C2\|OTOF\|NAB2\|APOLD1\|NR4A3\|FLNC\|CHRM4\|DDIT4\|ADAM21\|ARID5A\|KCNJ13\|ASGR1\|KNCN\|C17orf98\|KCNE2\|NMRK2\|EGR4\|C17orf50\|SLC6A20\|NFKBIA\|TMEM252\|GATSL3\|CHIA\|IL1B\|IGDCC3\|CCNO\|SPO11\|ATRIP\|OXGR1\|LAT\|SAMD14\|COL13A1\|FREM2\|KRT77\|WNK4\|CCDC67\|WFDC2\|C2orf74\|LGALS3\|LTB\|C10orf105\|FGL1\|TMPRSS11A\|TOMM6\|ADRA2A\|MARCKSL1\|NTSR1\|DND1\|SCN11A\|SOX8\|FZD2\|PDZD3\|OSR1\|SOCS3\|AMH\|SLC24A1\|EPS8L1\|GNB3\|KDM6B\|MXD3\|OXTR\|ARHGAP9\|SPEM1\|MSANTD1\|AIRE\|DUSP9\|LDOC1\|ATF3\|AMIGO3\|TCFL5\|PRKD2 |
| Prido Down Rett Up | 30 mg/kg BID | 2.081 | 3.10E−04 | 6.20E−04 | BMPER\|BEND5\|SDK1\|SORCS3\|TOX\|DEPTOR\|DPY19L1\|FANCF\|SKIDA1\|CHAC1\|PLCB4\|PTGFRN\|FGF22\|CDS1\|OSBPL3\|CBLN2\|RIMS3\|AKAP2\|RACGAP1\|MEDAG\|ZNF627\|SORL1\|CENPH\|FGF23\|GREB1\|ATOH7\|ASAP2\|HIST1H4C\|PATL2\|TMEM88\|PRICKLE1\|NPNT\|CMC2\|FIGNL1\|GALNT9\|RASGEF1B\|C11orf87\|DNAJC21\|HIST1H2BC\|BACH2\|CXCL6\|PLXDC1\|HIVEP1\|TSPAN5\|WEE1\|KHDRBS3\|IL17B\|CD40\|METTL18\|AGTR1\|C3orf80\|SSTR4\|COL15A1\|CITED4\|MAP10\|LDB2\|DYX1C1\|FBXW7\|HEBP2\|ADCY10\|PCDHA13\|PRR15\|PARVA\|PCSK1\|FSTL4\|SLCO4C1\|BST1\|SLC35G1\|ETV6\|STOX1\|HAPLN4\|ADRA1D\|ACSL5\|CD300LG\|PLCL2\|PCDHA11\|NRP1\|LRRK2\|B4GALNT3\|ZBP1\|PDIA5\|C14orf39\|FADD\|GFRA2\|ASPG\|IQGAP2\|NINJ2\|ASAP1\|GCNT4\|SULF2\|CDYL2\|BOK\|MBOAT4\|PHF11\|PKNOX1\|MYOCD\|COBL\|TSSK4\|PRSS23\|MURC\|FHOD3\|HS3ST2 |

NES-normalized enrichment score

Table 10 shows that pridopidine at both 3 and 30 mg/kg bid reverses the Rett gene expression pattern in the cortex in both directions (upregulates genes that are down in Rett mice vs WT and down regulates genes that are up in Rett mice vs WT).

The effect of pridopidine on the expression of genes downstream to the BDNF-TrkB pathway was assessed. Pridopidine 30 mg/kg bid significantly increases the expression of genes downstream to BDNF (Table 11).

TABLE 11

Pridopidine increases expression of genes downstream to BDNF

| Dose | NES | p.value | p.adjust | LeadingEdge |
|---|---|---|---|---|
| 30 mg/kg BID | 1.752 | 3.04E−03 | 4.44E−03 | Nab2\|Nr4a3\|Egr2\|Dusp5\|Fos\|Errfi1\|Per2\|Egr4\|Nab1\|Plk2\|Gadd45g\|Arc\|Klf10\|Klf5\|Baz1a\|Ier2\|Ptger4\|Cebpb\|Egr1\|Sertad1 |

NES-normalized enrichment score

Example 3: Pridopidine Improves Gait Function in Male MeCP2 Knock-Out (KO) Mouse Model of Rett Syndrome (Rett-KO)

Methods:

A colony of Rett model mice (Jackson Laboratories, Bar Harbor, ME; B6.129P2-Mecp2tm2Bird/J| Stock Number: 003890) was established by crossing heterozygous (het) females with wild type (WT) males (C57Bl/6J). Heterozygous MeCP2 Rett model mice (Rett-KO) and their wild-type (WT) littermates were housed in a temperature-controlled room between 20 and 23° C. with 50% humidity and a 12/12 light/dark cycle. The room temperature was maintained between 20 and 23° C. with a relative humidity maintained around 50%. Chow and water were provided ad libitum for the duration of the study. Additionally, upon initial observation of signs of hindlimb splay and/or locomotor difficulty, mice were provided with hydrogel daily.

After weaning, mice were single housed in OPTImice cages. All animals remained single housed during the remainder of the study. Mice were balanced and assigned to treatment groups, using baseline body weight and grip strength measures prior to start of study. All tests were performed during the animal's light cycle phase.

Pridopidine was evaluated at 30 mg/kg bid. Compound was dissolved in sterile DDW and administered orally twice a day (BID) at a dose volume of 10 mL/kg.

NeuroCube®—Gait Analysis

The NeuroCube® (NRC) system is one of PsychoGenics' proprietary technologies. It is a platform that employs computer vision to detect changes in gait geometry and gait dynamics in rodents. This platform is unique for gait testing for the following reasons:

It is completely automated and thus removes any bias or subjectivity

This system captures both gait geometry and gait dynamics (stance, swing, propulsion, etc)

The sensitivity of the computer vision and bioinformatics allow PsychoGenics to capture symptoms of the disease model earlier and more accurately.

Gait analysis was measured when mice were 5, 6 and 7 weeks of age. Mice are placed in the NeuroCube® for a 5 min test. The most dominant of the features that define the disease phenotype (symptom descriptors) were identified and ranked. Complex bioinformatic algorithms were employed to calculate the discrimination probability between the WT and the Rett mice, and also to detect the test compound's ability to reverse the disease phenotype.

Feature Analysis

Ranking is an important part of the analyses because it weighs each feature change by its relevance: if there is a significant change in some irrelevant feature measured for a particular phenotype, the low rank of this feature will automatically reduce the effect of such change in our analyses.

Relative difference (%) between feature values in two different sets is calculated and plotted in the order corresponding to feature ranks together with their ranks varying from 0 to 100%.

Feature Analysis—List of Features Analyzed

1) Average Speed: measurement of average speed to travel the length of the NRC.
2) Body Position: using paw imaging parameters measures X and Y body coordinates, X and Y paw coordinates, and paw directional vectors as they pertain to movement of the subject's body.
3) Gait: measurements of geometry (e.g. Stride Length, Step Length, Base Width) and dynamics (e.g. Stride Duration, Step Duration, Swing Duration) of gait.
4) Imaging: measurements of the paw contact area, perimeter of contact zone, and paw diameter (horizontal/vertical).
5) Paw Position: the position of each paw print relative to the center of the body is registered. The overlay of all recorded relative positions of the four paws creates four clusters of points (one for each paw). For each paw, the coordinate of the cluster center, its size, the number of paw prints, and relative geometry of clusters positioning are measured.
6) Rhythmicity: correlation coefficients between gait signals of each paw and all others: RF-LF, RF-LH, RF-RH, LH-RH, LH-RF, LF-RH, LH-RH; (F— forelimb; H—hindlimb; R—right; L—left)

Feature Analysis: Quantitative Assessment of the Disease Phenotype

Figure 1:
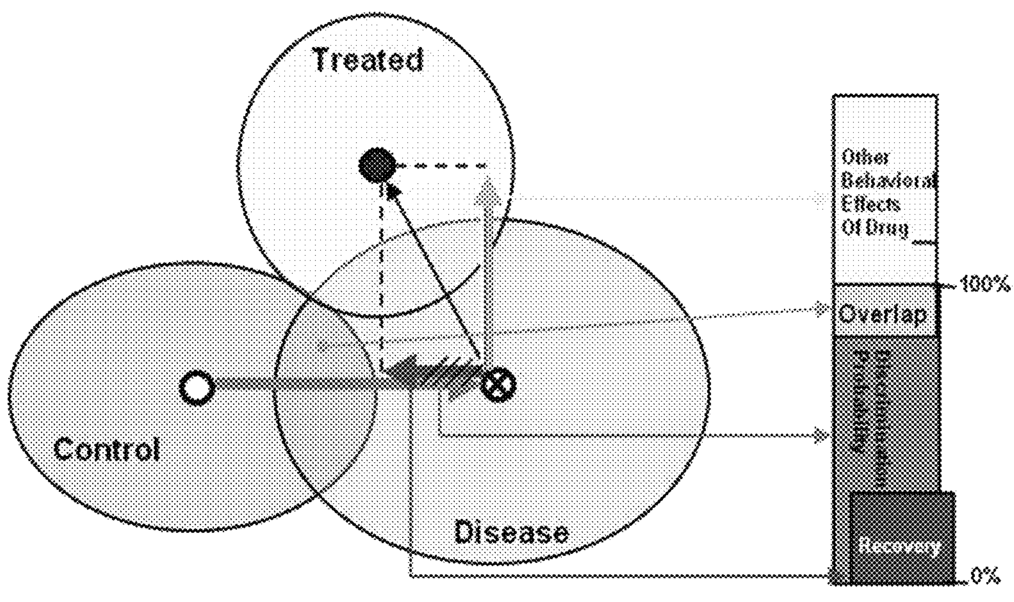
FIG. 1: Feature recovery as a measure of the therapeutic drug effect on Mecp2-KO Rett Syndrome model mice. This figure is intended to provide an explanation as to how the data is analyzed in FIGS. 4, 5 and 12.

In the feature space, the overlap between the "clouds" (Gaussian distributions approximating the groups of mice in the ranked de-correlated features space) serves as a quantitative measure of separability ("distinguishability") between the WT and Rett-KO mice (see FIG. 1). For visualization purposes, we plot each cloud with its semi-axes equal to the one standard deviation along the corresponding dimensions.

Feature Analysis: Drug-Induced Recovery

In the "recovery-due-to-the-drug" experiments the data are typically presented by the three Classes: WT, Rett-KO, and Rett-KO+pridopidine treatment ('treated').

Therefore, it is instructive to consider (and plot) the third group, treated, in the same coordinate system that best discriminates the other groups (WT and Rett) as shown in FIG. 1A.

Treatment Groups

The following treatment groups were used in this study

1. WT mice—Vehicle
2. Rett-KO (B6.129P2-Mecp2tm2Bird/J) mice—Vehicle
3. Rett-KO (B6.129P2-Mecp2tm2Bird/J) mice—pridopidine (30 mg/kg bid)

Statistical Analysis

Data were analyzed by repeated measures analysis of variance (ANOVA) followed by posthoc comparisons where appropriate. An effect was considered significant if $p<0.05$. Data are represented as the mean and standard error to the mean (s.e.m).

Results:

NeuroCube®

1. Gait Features

The discrimination plots of Rett-KO versus WT mice at 6 and 7 weeks of age are shown in FIG. 11A-11B. Feature name is a combination of parameter name and the paw name. FR—for limb, right; FL—fore limb, left; HR—hind limb, right; HL—hind limb, left.

Analysis of gait features indicate that Rett-KO mice show gait deficits compared to WT mice at both 6 and 7 weeks of age with the discrimination probability of 100% and 99%, respectively. At 6 and 7 weeks of age, Rett-KO mice show deficits in the gait measurements of geometry, primarily stride length, base width and step length, compared to WT mice.

The effects of Pridopidine (30 mg/kg bid) on gait deficits in Rett-KO mice were assessed when mice were 6 and 7 weeks of age. The summary of recovery is shown in FIG. 12. Pridopidine exhibits 44% and 100% recovery of gait deficits in Rett model mice at 6 and 7 weeks of age (both $p<0.05$, ANOVA).

Conclusions

Comparison of genotypes found that Rett-KO mice exhibit significant deficits in measurements of gait and compared to WT mice. The effects of chronic administration of Pridopidine (30 mg/kg/bid) in Rett-KO mice show significant gait recovery at 6 and 7 weeks.

Example 4: Pridopidine 45 mg Bid Improves Gait and Balance in Early HD Patients at 52 Weeks Change from baseline in UHDRS TMS gait and balances scale at weeks 26 and 52 in early HD (baseline TFC 7-13).

Table 2 (in the figure descriptions) and FIGS. 13A-13B show a trend towards improvement in UHDRS TMS gait and balance in early HD patients treated with pridopidine 45 mg bid compared to placebo at 26 and 52 weeks.

Early HD includes HD1 (TFC 11-13) and HD2 (TFC 7-10). FIG. 14B and table 3 (in the figure descriptions) show a significant effect of pridopidine 45 mg bid on change from baseline in gait and balance compared to placebo (p=0.0445) at 52 weeks. FIG. 14A shows a trend towards improvement at 26 weeks in pridopidine-treated HD1 patients. FIGS. 15A-15B and Table 4 (in the figure descriptions) display a trend towards improvement of pridopidine 45 mg bid on change from baseline in gait and balance compared to placebo in HD2 patients at both 52 and 26 weeks.

Example 5—Synergistic Effect of Pridopidine and Compound 1 or Pridopidine and Compound 4 on BDNF Secretion Compound 1 and Compound 4 both display a synergistic effect with pridopidine on BDNF secretion from B104 neuroblastoma cells.

Compound 1 and Compound 4 show selective binding to the Sigma-1 Receptor (S1R, Ki=0.37 μM for compound 1 and Ki=2.9 μM for compound 4) with no binding to the Sigma-2 receptor (S2R, Ki>100 μM for both compound 1 and 4), as shown in Table 12.

TABLE 12

Binding affinity of pridopidine, Compound 1 and Compound 4 to the Sigma-1 and Sigma-2 receptors

| Compound | S1R Ki (uM) | S2R Ki (uM) | S1R fold selectivity (S2R/S1R) |
|---|---|---|---|
| Pridopidine | 0.057 | 5.45 | 96 |
| Compound 1 | 0.37 | >100 | >270 |
| Compound 4 | 2.9 | >100 | >35 |

In-vitro binding assays performed at Eurofins Panlabs Taiwan, Ltd. Specific ligand binding was determined in the presence of an excess of unlabelled ligand. Inhibition constants (Ki) were calculated from in vitro binding assays using the Cheng Prusoff equation (Cheng and Prusoff 1973). Source: Johnston et al, 2019 (Johnston et al. 2019) and NC20-PHARM-2.

Thus, both Compound 1 and Compound 4 have high affinity to the S1R and no affinity (Ki>100) to the S2R.

Reductions in Brain-Derived Neurotrophic Factor (BDNF) levels play a key role in the pathogenesis of neurodegenerative and neurodevelopmental disorders and its levels are reduced in neurodegenerative and neurodevelopmental disorders such as Huntington disease (HD), Parkinson's disease, Alzheimer's disease (Zuccato and Cattaneo 2009) and Rett syndrome (Katz 2014).

Pridopidine demonstrates a dose dependent increase in BDNF secretion in rat neuroblastoma cells using an in-situ ELISA assay. This effect is mediated by activation of S1R, since pharmacological inhibition of the S1R abolished pridopidine's effect (Geva, Birnberg, et al. 2016).

When assessing the effect of Compound 1 or Compound 4 with pridopidine, the applicant identified an unexpected synergistic effect. The effect was observed in a BDNF in-situ ELISA assay (Geva, Kusko, et al. 2016).

Thus, the synergistic effect on BDNF release demonstrated below is directly relevant to the therapeutic effect of pridopidine and compound 1 and compound 4.

The following data surprisingly and unexpectedly show that pridopidine together with either Compound 4 or Compound 1 demonstrates a synergistic effect on BDNF release.

Synergistic Effect of Compound 4 and Pridopidine on BDNF Release

Pridopidine alone induces an increase in BDNF release of +13.6% at a concentration of 0.001 μM and +26% at a concentration of 0.005 μM, compared to control untreated cells. Compound 4 at a concentration of 0.001 μM alone has no effect on BDNF release compared to untreated control cells (−1.5%). However, pridopidine and Compound 4 together have an unexpected synergistic effect on BDNF release.

- Pridopidine 0.001 μM+Compound 4 at 0.001 μM induce a 59.1% increase in BDNF release compared to control untreated cells (FIG. 16A).
- Pridopidine 0.005 μM+Compound 4 at 0.001 μM induce an 80.7% increase in BDNF release compared to control untreated cells (FIG. 16B).

The effect of pridopidine and Compound 4 together is greater than the sum of the effects of each compound individually, indicating a surprising synergistic effect on BDNF secretion. The results are shown where the values are presented as percent (%) of change compared to untreated control.

Synergistic Effect of Compound 1 and Pridopidine on BDNF Release

Pridopidine alone at a concentration of 0.01 μM induces an increase in BDNF release compared to control untreated cells of +3.4%. Compound 1 alone at a concentration of 1 μM induces a +12.5% increase in BDNF release compared to control. However, pridopidine and Compound 1 together have a synergistic effect on BDNF release (+53.1%).

- Pridopidine (0.01 μM)+Compound 1 (1 μM) induce a 53.1% increase in BDNF release compared to control untreated cells (FIG. 17).

Again, these results indicate a surprising and unexpected synergistic effect of pridopidine and Compound 1 on BDNF secretion as their effect when administered together (+53.1%) is greater than the sum of the effects of each compound individually.

Thus, the applicant has shown that Compound 1 and Compound 4 have selective binding affinity to the S1R, together with a surprising and unexpected synergistic effect with pridopidine on BDNF release.

Example 6: Assessment of Efficacy of Pridopidine In Treating Patients Afflicted With RTT Periodically administering pridopidine and at least one of compounds 1-8 (e.g., daily or twice daily) intravenously or orally to a patient afflicted with Rett is effective to treat the patient.

Administering pridopidine effectively delays the onset of symptoms in the Rett patient.

Administering pridopidine effectively prevents or delays the worsening of, or improves at least one symptom in the Rett patient.

Administering pridopidine effectively prevents or delays the worsening of, or improves the mobility skill of the Rett patient. Administering pridopidine effectively prevents a partial or complete loss of acquired mobility skill of the Rett patient.

Administering pridopidine effectively prevents or delays the worsening of, or improves the gait of the Rett patient.

Administering pridopidine effectively prevents, delays or improves ataxia, apraxia, muscle weakness, spasticity, and/or rigidity in the Rett patient. Administering pridopidine effectively prevents, delays or improves impaired gait initiation in the Rett patient.

Administering pridopidine effectively prevents, delays or improves abnormal muscle tone, peripheral vasomotor disturbance, and/or scoliosis in the Rett patient.

Administering pridopidine effectively prevents or delays the worsening of, or improves purposeful hand skills in the Rett patient. Administering pridopidine effectively prevents, delays or improves abnormal hand movement, including but not limited to wringing, squeezing, clapping, washing, tapping, rubbing, and repeatedly bringing hands to mouth. Administering pridopidine effectively prevents a partial or complete loss of acquired purposeful hand skill of the Rett patient.

Administering pridopidine effectively prevents or delays the worsening of, or improves the communication skill of the Rett patient, including but not limited to speech and normal eye contact.

Administering pridopidine effectively prevents a partial or complete loss of acquired communication skill of the Rett patient.

Administering pridopidine effectively prevents, delays or improves growth retardation, seizure, cardiac abnormality, breathing irregularity, impaired sleeping pattern, bruxism while awake, decreased response to pain, hypotrophic cold blue feet, increased irritability, decreased alertness, decreased attention span, inappropriate laughing, and/or inappropriate screaming.

REFERENCES

Amaral, M. D., et al. (2007) “TRPC channels as novel effectors of BDNF signaling: Potential implications for Rett syndrome”. *Pharmacol Ther,* 113(2):394-409.

Cheng, Yung-Chi, and William H. Prusoff. 1973. “Relationship between the Inhibition Constant (KI) and the Concentration of Inhibitor Which Causes 50 percent Inhibition (150) of an Enzymatic Reaction.” Biochemical Pharmacology. https://doi.org/10.1016/0006-2952(73)90196-2.

CSID:25948790, www.chemspider.com/Chemical-Structure.25948790.html (accessed 23:27, July 2016).

CSID:7971505, www.chemspider.com/Chemical-Structure.7971505.html (accessed 23:33, Jul. 15, 2016).

Geva, Michal, et al. “Pridopidine activates neuroprotective pathways impaired in Huntington Disease.” Human molecular genetics 25.18 (2016): 3975-3987.

Guy J, Hendrich B, Holmes M, Martin J E, Bird A. (2001) A mouse MeCP2-null mutation causes neurological symptoms that mimic Rett syndrome. *Nat Genet.* 27(3): 322-326.

Isaias, L U., et al. (2014). “Gait Initiation in Children with Rett Syndrome.” *PLoS One,* 9(4): e92736.

Johnston, Tom H., Michal Geva, Lilach Steiner, Aric Orbach, Spyros Papapetropoulos, Juha-Matti Savola, Ian J. Reynolds, et al. 2019. “Pridopidine, a Clinic-Ready Compound, Reduces 3,4-Dihydroxyphenylalanine-Induced Dyskinesia in Parkinsonian Macaques.” Movement Disorders, December. https://doi.org/10.1002/mds.0.27565.

Katz, D M. 2014. “Brain-Derived Neurotrophic Factor and Rett Syndrome.” Handbook of Experimental Pharmacology 220: 481-95. https://doi.org/10.1007/978-3-642-45106-5_18.

Pozzo-Miller, L., Pati S., & Percy, A. K. (2015). “Rett Syndrome: Reaching for Clinical Trials.” *Neurotherapeutics,* 12(3):631-40.

Smith-Dijak, A. I., Nassrallah, W. B., Zhang, L. Y., Geva, M., Hayden, M. R., & Raymond, L. A. (2019). Impairment and restoration of homeostatic plasticity in cultured cortical neurons from a mouse model of huntington disease. Frontiers in cellular neuroscience, 13, 209.

Sandweiss A J, Brandi N T, Zoghbi H Y (2020) “Advances in understanding of Rett syndrome and MECP2 duplication syndrome: prospects for future therapies”. Lancet Neurol. August; 19(8):689-698.

Weng, S. M. et al. (2011). “Rett Syndrome: From Bed to Bench.” *Pediatrics and Neonatology,* 52:309-316.

Xu X, Pozzo-Miller L. EEA1 restores homeostatic synaptic plasticity in hippocampal neurons from Rett syndrome mice. J Physiol. 2017 Aug. 15; 595(16):5699-5712.

Zuccato, Chiara, and Elena Cattaneo. 2009. “Brain-Derived Neurotrophic Factor in Neurodegenerative Diseases.” Nature Reviews Neurology 5 (6): 311-22. https://doi.org/10.1038/nrneuro1.2009.54.

What is claimed is:

1. A method for treating a Rett Syndrome in a subject in need thereof comprising administering a composition comprising pridopidine or a pharmaceutically acceptable salt thereof and at least one of compounds 1-8:

(Compound 1)

(Compound 2)

(Compound 3)

(Compound 4)

(Compound 5)

(Compound 6)

-continued (Compound 7)

or (Compound 8)

or pharmaceutically acceptable salt thereof so as to thereby treat the subject.

2. The method of claim 1, wherein the method delays worsening or improves at least one symptom of Rett syndrome in the subject, wherein the symptom is abnormal gait, ataxia, impaired gait initiation delay in acquiring purposeful hand skills or a partial or complete loss of acquired purposeful hand skills, or the symptom is abnormal hand movement, startle response or delayed crawling, and/or walking; decreased ability to crawl, and/or walk; or abnormal eye movement.

3. The method of claim 1, wherein the pharmaceutically acceptable salt of pridopidine is hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, the naphthalene-2-sulphonate, phthalate, salicylate, sorbate, stearate, succinate, tartrate or toluene-p-sulphonate salt.

4. The method of claim 1, wherein the pharmaceutically acceptable salt of Compounds 1-8 is hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, the naphthalene-2-sulphonate, phthalate, salicylate, sorbate, stearate, succinate, tartrate or toluene-p-sulphonate salt.

5. The method of claim 1, wherein the composition is administered orally, nasally, inhaled, by subcutaneous injection, or through an intravenous, intraperitoneal, intramuscular, intranasal, buccal, vaginal, rectal, intraocular, intrathecal, topical or intradermal route.

6. The method of claim 3, wherein the composition is administered orally.

7. The method of claim 1, wherein the composition is administered in the form of an aerosol, an inhalable powder, an injectable, a liquid, a gel, a solid, a capsule or a tablet.

8. The method of claim 6, wherein the composition is administered orally and formulated as a tablet, a capsule, a pill, a powder, multipaticulates in capsule or sachet, liquid solution or as a liquid suspension.

9. The method of claim 1, wherein the pharmaceutical composition is administered less often than once daily.

10. The method of claim 1, wherein the pharmaceutical composition is administered once daily or twice daily.

11. The method of claim 1, wherein the pridopidine is administered in a daily dose of between 0.5 mg/day-315 mg/day.

12. The method of claim 1, wherein the pridopidine is administered in a daily dose of between 0.5 mg/day-45 mg/day.

13. The method of claim 1, wherein the pridopidine is administered in a daily dose of between 10 mg/day-100 mg/day.

14. The method of claim 1, wherein the pridopidine is administered in a daily dose of 45 mg/day-90 mg/day.

15. The method of claim 1, wherein the pridopidine is administered in a daily dose of 45 mg/day-180 mg/day.

16. The method of claim 1, wherein the composition is administered in one dose or two doses per day.

17. The method of claim 1, wherein the composition comprises pridopidine or a pharmaceutically acceptable salt thereof and at least one of compound 1, compound 4, pharmaceutically acceptable salt thereof or combination thereof.

18. The method of claim 1, wherein the composition comprises pridopidine or a pharmaceutically acceptable salt thereof and compound 1 or pharmaceutically acceptable salt thereof.

19. The method of claim 1, wherein the composition comprises pridopidine or a pharmaceutically acceptable salt thereof, compound 1 and compound 4 or pharmaceutically acceptable salt thereof.

20. The method of claim 1, wherein the weight ratio between the pridopidine and at least one of compounds 1-8 is in the range of 1:0.0001 to 1:0.1.

21. The method of claim 20, wherein the weight ratio between the pridopidine and at least one of compounds 1-8 is in the range of 1:0.005 to 1:0.1.

22. The method of claim 20, wherein the weight ratio between the pridopidine and at least one of compounds 1-8 is in the range of 1:0.005 to 1:0.005.

23. The method of claim 2, wherein the abnormal hand movement is wringing, squeezing, clapping, washing, tapping, rubbing, and/or repeatedly bringing hands to mouth.

24. The method of claim 2, wherein the abnormal eye movement is prolonged staring, excessive blinking, crossed eyes, and/or closing one eye at a time.

25. The method of claim 2, wherein the composition improves the symptom by at least 20%, at least 30%, at least 50%, at least 80%, or 100%.

26. The method of claim 1, wherein the composition is administered in an amount effective to increase or maintain the BDNF serum level in the subject and/or to increase the BDNF brain levels in the subject afflicted with Rett Syndrome.

27. The method of claim 1, wherein the subject has a mutation in at least one of the methyl CpG binding protein 2 (MeCP2) gene, the cyclin-dependent kinase-like 5 (CDKL5) gene or the Forkhead box protein G1 (FOXG1) gene.

* * * * *